United States Patent
Archer et al.

(10) Patent No.: US 9,440,849 B2
(45) Date of Patent: Sep. 13, 2016

(54) NANOPARTICLE ORGANIC HYBRID MATERIALS (NOHMS)

(75) Inventors: Lynden A. Archer, Ithaca, NY (US); Laura Lynne Olenick, Canonsburg, PA (US); Jennifer Lyn Schaefer, Groton, NY (US); Alexandra Elena Corona, Westminste, CA (US)

(73) Assignee: Cornell University, Ithaca, NY (US)

( * ) Notice: Subject to any disclaimer, the term of this patent is extended or adjusted under 35 U.S.C. 154(b) by 825 days.

(21) Appl. No.: 13/144,431

(22) PCT Filed: Jan. 15, 2010

(86) PCT No.: PCT/US2010/000089
§ 371 (c)(1),
(2), (4) Date: Oct. 27, 2011

(87) PCT Pub. No.: WO2010/083041
PCT Pub. Date: Jul. 22, 2010

(65) Prior Publication Data
US 2012/0039824 A1    Feb. 16, 2012

Related U.S. Application Data

(60) Provisional application No. 61/193,984, filed on Jan. 15, 2009.

(51) Int. Cl.
*H01M 10/40* (2006.01)
*B82Y 30/00* (2011.01)
(Continued)

(52) U.S. Cl.
CPC .............. *B82Y 30/00* (2013.01); *A61K 9/5115* (2013.01); *A61K 9/5192* (2013.01); *C08K 9/06* (2013.01);
(Continued)

(58) Field of Classification Search
CPC .......... H01M 10/056; A61K 8/89; C07F 7/02
USPC .................. 429/199; 428/407; 427/212, 215; 424/9.3, 59, 463, 490
See application file for complete search history.

(56) References Cited

U.S. PATENT DOCUMENTS

2002/0134006 A1   9/2002   Malfer et al.
2003/0170313 A1*  9/2003   Prokop ......................... 424/490
(Continued)

FOREIGN PATENT DOCUMENTS

| CN | 101220128 A | 7/2008 |
|---|---|---|
| KR | 10-2008-0074410 | 8/2008 |
| WO | 2006110166 | 10/2006 |

OTHER PUBLICATIONS

"Ethomeen 18/25", Guide chem Chemical Tracking Guide, retrieved on Jul. 22, 2014 from: http://www.guidechem.com/cas-266/26635-92-7.html.*

(Continued)

Primary Examiner — Kenneth Douyette
(74) Attorney, Agent, or Firm — Hodgson Russ LLP

(57) ABSTRACT

A nanoparticle organic hybrid material (NOHM) containing an organic polymeric corona having a molecular weight in a range of 100-50,000 g/mol, wherein the organic polymeric corona is covalently attached to an inorganic nanoparticle core, wherein the NOHM exhibits liquid-like properties so that the NOHM moves freely and flows in a manner so that when the NOHM is in a container, the NOHM takes the shape of the container, and wherein the NOHM has a volume fraction (fc) of the inorganic particle ranging from about 0.05 to 0.75, methods of making the NOHMs, and compositions containing the NOHMs.

12 Claims, 10 Drawing Sheets

(51) Int. Cl.
*A61K 9/51* (2006.01)
*C08K 9/06* (2006.01)
*C10M 171/06* (2006.01)
*H01M 10/05* (2010.01)
*C08K 3/08* (2006.01)
*C08K 3/22* (2006.01)

(52) U.S. Cl.
CPC ............. *C10M 171/06* (2013.01); *C08K 3/08* (2013.01); *C08K 3/22* (2013.01); *C10N 2220/021* (2013.01); *C10N 2220/082* (2013.01); *C10N 2220/084* (2013.01); *C10N 2250/12* (2013.01); *H01M 10/05* (2013.01)

(56) References Cited

U.S. PATENT DOCUMENTS

2005/0058603 A1   3/2005  Gao et al.
2005/0221431 A1*  10/2005 Backer et al. ............ 435/69.1
2008/0075667 A1   3/2008  Berkland et al.
2008/0097280 A1   4/2008  Martin et al.
2008/0234149 A1   9/2008  Malshe et al.

OTHER PUBLICATIONS

"Different Solvent Free Synthetic Routes to Organic/Inorganic Hybrid Materials", Kaddami et al., MRS Proceedings, vol. 576 / 1999. p. 51-61.*

Robert Rodriguez et al: "Nanoscale Ionic Material", Advanced Materials, vol. 20, No. 22, pp. 4353-4358. Nov. 18, 2008.

Jyongsik Jang et al: "Synthesis and characterization of monodisperse silica-ployaniline core-shell nanoparticles", Chemical Communications, No. 15, p. 1622. Jan. 1, 2006.

Ivan Sondi et al: "Encapsulation of Nanosized Silica by in Situ Polymerization of tert-Butyl Acrylate Monomer +", Langmiur, vol. 16, No. 23, pp. 9031-9034. Nov. 1, 2000.

Lizhong Jiang et al: "Synthesis and characterization of stimuli-responsive poly(acrylic acid) grafted silica nanoparticles", Smart Materials and Structures, vol. 16, No. 6, pp. 2169-2174. Dec. 1, 2007.

* cited by examiner

NANOPARTICLE ORGANIC HYBRID MATERIALS (NOHMS)

FIELD OF THE INVENTION

The present invention relates to nanoparticle organic hybrid materials (NOHMs), methods of making NOHMs, and compositions containing NOHMs.

BACKGROUND OF THE INVENTION

Organic hybrid materials contain both organic and inorganic components. The presence of these organic and inorganic components impart some unusual properties to the materials (e.g. high modulus and high toughness; inherent flame retardance; enhanced gas barrier properties). As a result, organic hybrid materials have captured the interest of a number of industries. However, the manufacturing and use of organic hybrid materials present a number of challenges to the skilled artisan, as these materials often exhibit poor dispersion, miscibility, and interfacial strength between inorganic nanostructures and organic polymers.

The inventors of the present application have discovered nanoscale organic hybrid materials which overcome these shortcomings.

SUMMARY OF THE INVENTION

A first embodiment of the invention is a nanoparticle organic hybrid material (NOHM), comprising an organic polymeric corona having a molecular weight in a range of 100-50,000 g/mol, wherein the organic polymeric corona is attached to an inorganic nanoparticle core, wherein the NOHM exhibits liquid-like properties so that the NOHM moves freely and flows in a manner so that when the NOHM is in a container the NOHM takes the shape of the container, and wherein the NOHM has a volume fraction $f_c$ of the inorganic particle ranging from about 0.05 to 0.75.

A second embodiment is a method for producing a NOHM, comprising attaching an organic polymeric corona having a molecular weight in a range of 100-50,000 g/mol to an inorganic polymeric corona to obtain a NOHM of the first embodiment.

A third embodiment of this invention is a composition comprising the NOHM of the first embodiment.

A "corona" as recited herein is an organic polymer.

The phrase "the order of magnitude" as recited herein means the critical molecular weight or degree of polymerization below a critical value can be estimated within a factor of ten.

A "star polymer" recited herein means a polymer with a chain architecture that is composed of at least several branched arms that are combined together through a single joint point or multiple joint points.

The term "hyper-branched polymer" recited herein means chain architectures with multiple branches jointed together in a compact but irregular way.

The term "comb" recited herein means a type of star polymer having chain architecture for a polymer with multiple branches equally distributed along a backbone.

A "dendrimer" as recited herein is a polymer that is branched. This tends to reduce intermolecular chain entanglement and crystallization.

The phrase "newtonian fluid" as recited herein means a fluid or dispersion whose rheological behavior is described by Newton's law of viscosity. Here shear stress is proportional to shear rate, with the proportionality constant being the viscosity.

Viscosity ('thickness') is the term that describes resistance to flow. High viscosity liquids are relatively immobile when subjected to shear (a force applied to make them move), whereas low viscosity fluids flow relatively easily. Measurement of viscosity, and other rheological properties, can be made using either capillary or rotational rheometers, the choice of system depending on the properties of the material being tested and the data required.

The term "shear" as recited herein means the rate of deformation of a fluid when subjected to a mechanical shearing stress.

A "shear stress" as recited herein means an applied force per unit area needed to produce deformation in a fluid.

The phrase "yield stress" as recited herein means the applied stress that must be exceeded in order to make a structured fluid flow. Approximate yield stress measurements can be gained by plotting the shear stress values for a range of shear rates, fitting a curve to the data, and extrapolating through the stress axis. The intersect on the stress axis provides the yield stress. An alternative method for obtaining yield stresses is to use a static vane-based test method. The vane is lowered into the undisturbed sample and then torqued slowly. The sample deforms elastically as the imposed stress increases until a yield stress is attained. At this point the sample starts to flow significantly and the measured stress falls from a peak.

A "random coil" as recited herein means a polymer conformation where the monomer subunits are oriented randomly while still being bonded to adjacent units. It is not one specific shape, but a statistical distribution of shapes for all the chains in a population of macromolecules. The conformation's name is derived from the idea that, in the absence of specific, stabilizing interactions, a polymer backbone will "sample" all possible conformations randomly. Many linear, unbranched homopolymers in solution or above their melting temperatures assume (approximate) random coils. Even copolymers with monomers of unequal length will distribute in random coils if the subunits lack any specific interactions. The parts of branched polymers may also assume random coils.

The phrase "self-solvated" as recited herein means a NOHM solution where no solvent is present.

A "monodisperse corona" as recited herein is an organic polymeric corona having a polydispersity index (PDI) less than 1.3.

A "polydisperse corona" as recited herein is an organic polymeric corona having a PDI greater than 1.3.

The "PDI" as recited herein is a measure of the distribution of molecular mass in a given polymer sample. The PDI calculated is the weight average molecular weight divided by the number average molecular weight. It indicates the distribution of individual molecular masses in a batch of polymers. The PDI has a value equal to or greater than 1, but as the polymer chains approach uniform chain length, the PDI approaches unity. For some natural polymers PDI is almost taken as unity. The PDI from polymerization is often denoted as:

$$PDI=M_w/M_n.$$

In one aspect of this embodiment, the phrase "high grafting density" as recited herein means that organic polymeric coronas are attached to an inorganic nanoparticle core in a range of 1 to 10 molecules per square nanometer, and preferably 1 to 5 molecules per square nanometers.

"Bulk polymerization" as recited herein means the formation of polymer from substantially undiluted monomers. Incidental amounts of solvents, coalescents, plasticizers and/or water may also be present. Further description is given in "Bulk Polymerization", *Encyclopedia of Polymer Science and Engineering*, Vol. 2, pp. 500-514 (1989), the disclosure of which is incorporated herein by reference.

"Solution polymerization" as recited herein means a polymerization technique in which both the monomers and resultant polymer are substantially soluble in a diluent (e.g., organic solvents, coalescents, plasticizers and/or water) that is also present. It is described in "Solution Polymerization", *Encyclopedia of Polymer Science and Engineering*, Vol. 15, pp. 402-418, (1989), the disclosure of which is incorporated herein by reference.

"Dispersion polymerization" as recited herein means a polymerization technique in which polymerization of the monomers is at least initially carried out by bulk or solution polymerization, with the reaction system thereafter being emulsified or dispersed in an aqueous medium. It includes polymerization reactions in which polymerization is carried out to substantial or total completion before the bulk or solution polymerization system is dispersed in the aqueous medium.

"Emulsion polymerization" as recited herein means a polymerization technique in which the monomers are emulsified in an aqueous medium containing a water-soluble initiator. Polymerization occurs predominantly in micelles formed by surfactant and not in the initially formed monomer droplets. The latter serve merely as a reservoir of monomers which diffuse out to find micelles and swell them. This mechanism produces polymer particles which are significantly smaller than original monomer droplets.

The "molecular weight" as recited herein can be determined by using gel permeation chromatography (GPC) with a polystyrene standard.

DETAILED DESCRIPTION OF THE INVENTION

Figure 1:
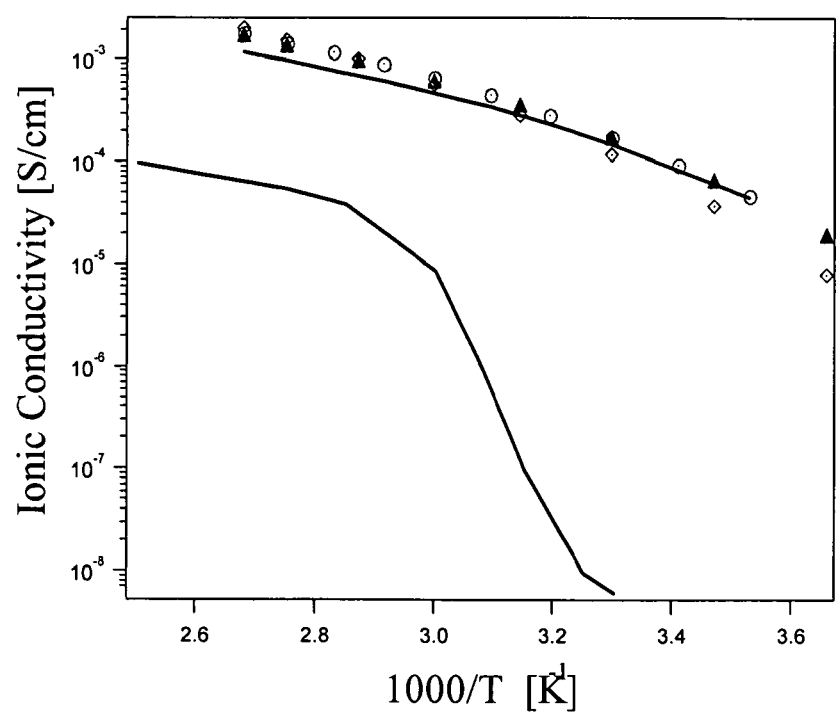
FIG. 1 shows the ionic conductivities of NOHMs and polymer electrolytes as a function of reciprocal temperature. Circles fc=0.2, triangle fc=0.28, diamond fc=0.35.

We turn now to the first embodiment.

A feature of this embodiment is a nanoparticle organic hybrid material (NOHM), comprising an organic polymeric corona or arm having a molecular weight in a range of 100-50,000 g/mol, wherein the organic polymeric corona is attached to an inorganic nanoparticle core. The NOHMs have a volume fraction (f$_c$) of the inorganic particle ranging from about 0.05 to 0.74. The NOHMs exhibit liquid-like properties so that the NOHM moves freely and flows in a manner so that when the NOHM is in a container the NOHM takes the shape of the container in the absence of a suspending solvent. In other words, NOHMS are in the form of a self-suspended, suspension, wherein the particles are loose and can form a distinct surface at the boundaries of its bulk material. A force equal to or slightly greater than the yield stress is optionally applied when NOHMs are placed in the container so that the NOHMs takes the shape of the container.

The organic polymeric coronas are comprised of a single polymer segment or may include multiple blocks from different monomers. In other words, the organic polymeric coronas of the present invention are homopolymers and copolymers. The organic polymeric corona is a linear, branched, hyper-branched, or comb polymer.

Examples of polymeric materials useful for the organic polymeric coronas include, by way of example and without limitation, polyethers, polyesters, polyamides, polysiloxanes, polysulfides, polysulfonates, polysulfonamides, poly(thiol ester)s, polyamines, and the like. Preferred organic polymeric coronas are ethylene carbonate (EC), propylene carbonate (PC), cis-1,4-isoprene (PI), ethylene vinyl acetate (EVA), poly vinyl chloride (PVC), poly(ethylene glycol) (PEG), poly(ethylene oxide) (PEO), polyoxyethylene (POE), polydimethylsiloxane (PDMS), poly-alpha-olefin (PAO), polyvinylidene fluoride (PVDF), PEG-PS diblock copolymer, or a combination thereof. The organic polymeric coronas have a molecular weight in one of the following ranges 100-50,000 g/mol; 100-20,000 g/mol; 100-10,000 g/mol; 100-5,000 g/mol; 250-7,500 g/mol; 500-7,500 g/mol; 500-5,000 g/mol; 250-2,500 g/mol; 250-1,500 g/mol; and 100-2,500 g/mol. These organic polymeric coronas preferably have a molecular weight of 100-1,000 g/mol.

In one aspect of this embodiment, at least two different organic polymeric coronas are tethered to an inorganic nanoparticle core of a NOHM. The NOHM comprises a first organic polymeric corona and a second organic polymeric corona. For example, the first organic polymeric corona is selected from the group consisting of EVA, PVC, PEG, PEO, POE, PDMS, PAO, and PVDF and the second organic polymeric corona is selected from the group consisting of EVA, PVC, PEG, PEO, POE, PDMS, PAO, and PVDF. In yet another example, an inorganic nanoparticle core of a NOHM is tethered to a first organic polymeric corona composed of PEG and a second organic polymeric corona composed of PEO. These types of NOHMs still exhibit liquid-like so that the NOHM moves freely and flows in a manner so that when the NOHM is in a container, the NOHM takes the shape of the container in the absence of a suspending solvent, as discussed above.

The number of organic polymeric arms attached to the inorganic nanoparticle core chains can vary from 1-750, 1-250, 250-750, 250-700, 350-700, or 375-675.

In another feature, the end groups of the organic polymeric coronas are functionalized. Examples of functionalized groups on the organic polymeric coronas are nitroxy, alkene, alkyne, epoxy, ethylene oxide, chloride, bromide, amine, sulfonic acid, hydroxylcarboxyl, anhydride, fluorine, sulfonate esters, amino, hydrazido, mercpato, carbonate, carbamate, chlormate, cyanuryl chloride, epoxide, aldeyhde, or siloxane (See e.g., see Zalipsky, Functionalized Poly (ethylene glycol) for Preparation of Biologically Relevant Conjugates, *Bioconjugate Chem* 9. 195, 6, 150-165, the entirety of which is hereby incorporated by reference. The organic polymeric coronas are functionalized to impart certain properties to the NOHM, and/or to carry out further chemical reactions.

The organic polymeric coronas of the NOHMs are tethered to an inorganic nanoparticle core and are produced as discussed in detail below. An one aspect of this embodiment is that the NOHMs do not contain any ionic bonds and the organic polymeric coronas are covalently attached to the inorganic nanoparticle cores.

A variety of inorganic nanoparticles can be used for the core. A nanoparticle is a small object that behaves as a whole unit in terms of its transport and properties. Nanoparticles generally measure in at least one dimension between 1-1,000 nanometers (nm), preferably 1-500 nm, and more preferably 1-100 nm. Nanoparticles have a very high surface area to volume ratio that provides numerous opportunities to attach organic polymeric coronas on the surface of the nanoparticles. Extensive libraries of nanoparticles, composed of an assortment of different sizes, shapes, and materials, and with various chemical and surface properties, have been constructed. In this regard, a variety of nanoparticles can be used as cores, including multi-lobed nanoparticles, conductive nanoparticles, hollow nanoparticles, quantum dots, nanocrystals, magnetic nanoparticles, metal nanoparticles, metal oxide nanoparticles, and nanorods.

The nanoparticles are selected from a variety of materials including those selected from the group consisting of metal oxide (e.g., $SiO_2$, $SnO_2$, $Fe_2O_3$, $Fe_3O_4$, $CO_3O_4$, MgO, SrO, BaO, CaO, $TiO_2$, $ZrO_2$, FeO, $V_2O_3$, $V_2O_5$, $Mn_2O_3$, NiO, CuO, $Al_2O_3$, $SiO_2$, ZnO, $Ag_2O$), and metals (e.g., Y, Zr, La, Ce, Mg, Sr, Ba, Ca, Ti, Zr, Fe, V, V, Mn, Fe, Ni, Cu, Al, Si, Zn, Ag, Au, Co), and metal salts. Metal oxides includes both oxides, metal hydroxides, metal hydrated oxides, metal oxohydroxides, or metal oxoperoxohydroxides. This also includes precursor materials such as nitrates, carbonates and acetates which can be converted to their corresponding metal oxides by heat treatment.

In another aspect of this invention, the inorganic nanoparticle cores comprise 5-74%; 50-74%; 5-50%; 10-35%; 5-25%; and 10-25% by volume of the NOHM. NOHMS having high inorganic nanoparticle core contents display properties similar to glasses, stiff waxes, and gels. NOHMs having low inorganic nanoparticle core contents generally form particle-based neat fluids, characterized by transport properties (viscosity, ionic conductivity) similar to Newtonian liquids comprised of molecular building-blocks. This conductivity is measured from the dielectric loss using a dielectric spectrometer and the viscosity is measured using a rheometer or viscometer.

In this regard, another feature of this embodiment is that the NOHMs have a volume fraction (fc) of the inorganic nanoparticle core greater than 0.05, 0.1, 0.2, or 0.3. In another feature of this embodiment, the NOHMs have a $f_c$ of the inorganic particle ranging from about 0.05 to 0.74, preferably 0.1 to 0.62, more preferably greater than 0.1 to and less than 0.52, and even more preferably 0.1 to 0.5. In NOHMs having a fc greater than 0.1, the cores begin to percolate (i.e. exhibit connectivity/cooperativity) up the macroscopic scale, but aggregation of the cores is inhibited by the tethered organic polymeric corona.

The effects of volume fraction on viscosity are described using the Krieger-Dougherty equation:

$$\frac{\eta}{\eta_{medium}} = \left(1 - \frac{\phi}{\phi_m}\right)^{-[\eta]\phi_m}$$

where $\eta$ is the viscosity of the suspension, $\eta$medium is the viscosity of the base medium, $\phi$ is the volume fraction of solids in the suspension, $\phi_m$ is the maximum volume fraction of solids in the suspension and $[\eta]$ in the intrinsic viscosity of the medium, which is 2.5 for spheres. This correlation shows a general increase in viscosity with increasing volume fraction. As the volume fraction of solids in the system goes up: the particles generally become more closely packed together; it becomes more difficult for them to move freely; particle-particle interactions increase; and resistance to flow (viscosity) rises. As the volume fraction nears maximum for the sample, viscosity rises very steeply.

In another aspect of this embodiment, the random-coil size of the organic polymeric coronas is the same size or within 10%, preferably 5% and more preferably within 2.5% of a diameter of the inorganic nanoparticle core. When the random-coil size of the tethered oligomers (corona) are of a comparable size to a diameter of the inorganic nanoparticle core, NOHMs manifest excellent stability against aggregation and exhibit rheological features characteristic of a soft-glassy solid.

NOHMs of this embodiment exhibit unusual physical properties, e.g. high mechanical modulus, hardness, lithium intercalation efficiency, high refractive index, large heat capacity, high electrical/thermal conductivity, normally only seen in inorganic materials and exert a measurable influence upon the behavior of the NOHM or a composition comprising the NOHM.

We turn now to the second embodiment

A second embodiment is a method for producing, comprising attaching an organic polymeric corona having a molecular weight in a range of 100-50,000 g/mol to an inorganic polymeric corona to obtain a NOHM of the first embodiment. In one feature of this embodiment, the organic polymeric corona is attached to the inorganic nanoparticles core via a covalent bond and the NOHM does not contain any ionic bonds.

The organic polymeric coronas used in accordance with this embodiment can be produced by a variety of techniques known to those skilled in the art, including bulk, solution, dispersion, emulsion, condensation, anionic, free-radical and living radical polymerizations (e.g., see Morrison and Boyd, *Organic Chemistry*, the entirety of which is incorporated by reference).

Likewise, the NOHMs of the first embodiment can be produced by a variety of techniques known to those skilled in the art.

One approach for producing the NOHMs of the first embodiment is the "graft-to" methodology, which involves the reaction of pre-synthesized polymer molecules of controlled molecular weight (i.e., a molecular weight of 100-50,000 g/mol) bearing reactive groups at one or both ends of the chain with complementary functional groups naturally present on or introduced onto the core (see e.g., Jang, J.; Ha, J.; Kim, B., Synthesis and characterization of monodisperse silica-polyaniline core-shell nanoparticles. *Chemical Communications* 2006, 1622-1624).

In this approach, sterics play an important role in the graft density of the polymer on the core. For example, a polymer with a high molecular weight may only be able to attach to a few places on the core before the sterics of the molecules block any further reactions. In this regard, the use of organic polymeric coronas having a low molecular weight (e.g., 100-50,000 g/mol) and as discussed above is preferable as such organic polymeric coronas will not be affected as much by the sterics of the molecules and will exhibit a higher graft density than an organic polymeric corona having a higher molecular weight. The main benefit to this approach is the ability to synthesize the polymer to a low polydispersity index (PDI). Another benefit is the control over the molecular weight of the polymer which can be exercised.

For example, NOHMs are produced by dispersing a reactive polymer and an inorganic nanoparticle within the same solution. For example, organic polyether polymers containing a terminal reactive functional group (e.g. alkoxysilane-PEG-OH, alkoxysilane-PEG-epoxide) are dissolved in water to form a dilute polymer solution. The precursor core particles, stored in the form of an aqueous suspension stabilized by dissociable cations (e.g. $Na^+$ or $NH_4^+$), is diluted with an aqueous solution. Temporary hydrogen bonds are created between the organic polymer and hydroxyl groups that have formed at the surface of the inorganic nanoparticle. The temporary bonds can then be cured between the inorganic nanoparticle core and organic polymeric corona, resulting in permanent covalent bonds (e.g., see example 1).

Scheme 1 illustrates this approach as follows:

with a small molecule initiator. This initiator is able to bind to the core with a higher graft density than a functionalized polymer. The core-initiator molecule is then used as an initiator for controlled living polymerization (CLP). The CLP process utilized is preferably atom transfer radical polymerization (ATRP) as described by Zhang et al., Synthesis and Characterization of Polymer Brushes Containing Metal Nanoparticles. *Polymer Bulletin*, 57, 253-259, (2006).

Yet another benefit of using ATRP over other living radical polymerizations is that the use of the catalyst (e.g., the 2-bromoisobutyrl bromide, CuBr/tris[2-pyridyl)methyl]amine or CuBr/tris[2-pyridyl)ethyl]amine) inhibit biomolecular termination events, whereby each monomer to the propagating species is "capped" with a halogen atom that has been transferred from the catalyst. This capping, which is reversible, assures that the propagating radical species will not interact with each other, terminating the reaction. The deactivation of the propagating species allows for more control over molecular weights and molecular weight dispersities (see Kamigaito, M.; Ando, T.; Sawamoto, M., Metal-Catalyzed Living Radical Polymerization. *Chemical Reviews* 2001, 101, 3689-3745).

ATRP has been used to polymerize a variety of monomers, such as methacrylates, acrylates, styrenes, acrylonitrile, dienes, acrylamides, methylacrylamides as discussed in Matyjaszewski et al., Atom Tranfer Radical Polymerization. *Chemical Reviews*, 101, 2921-2990, (2001), the entirety of which is hereby incorporated by reference. The catalyst system, which includes a halogenated metal coupled with a ligand, is tailored to fit these monomers. In choosing the appropriate catalytic system, the monomer, polymer solubility, halogenated metal solubility, the redox potential of the catalyst system, and the activity of the carbon-halogen bond in the initiator and monomer are all considered. For a catalyst system to be effective, the lower oxidation state of

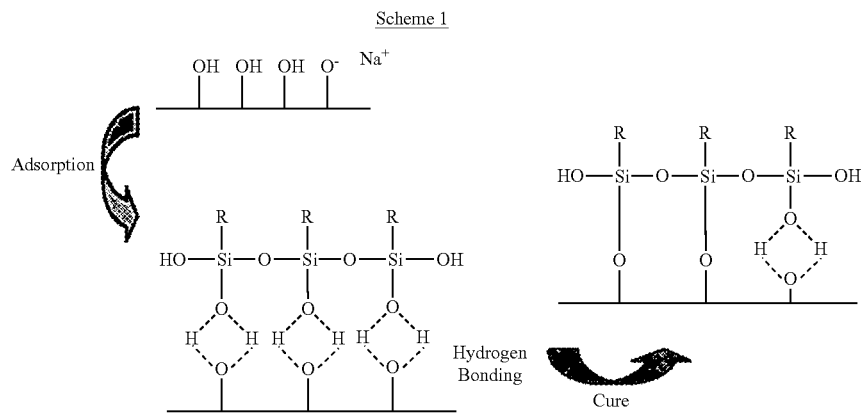

Scheme 1

The Krieger-Dougherty model as discussed above is used to predict the solubility of the NOHMs. The ability to predict the relative viscosity of NOHMs using this straightforward extension of the Krieger-Dougherty suspension model confirms that NOHMs are self-suspended, sterically-stabilized suspensions of nanoparticles.

Another approach for producing NOHMs of the first embodiment is the "grow from" approach as discussed in Matyjaszewski et al., Atom Tranfer Radical Polymerization. *Chemical Reviews* 2001, 101, 2921-2990. Zhang, et al., Synthesis and Characterization of Polymer Brushes Containing Metal Nanoparticles, *Polymer Bulletin*, 57, 253-259 (2006). In this approach, the inorganic core is first reacted the metal center should be more stable than the higher oxidation state so that there exists a low concentration of the radical species (see e.g., Kamigaito, M.; Ando, T.; Sawamoto, M., Metal-Catalyzed Living Radical Polymerization. *Chemical Reviews* 2001, 101, 3689-3745).

Polymerization rates and molecular weight dispersities are also improved by additives and the use of additives should be taken into account if the needed catalytic system for the chosen monomer does not produce the desired result. For example, the additive, $Al(Oi-Pr)_3$, has been used to stabilize higher oxidation states of the metal complex to aid in the radical generation from a dormant species as disclosed in Ando, T.; Kamigaito, M.; Sawamoto, M., Metal Alkoxides as Additives for Ruthenium(II)-Catalyzed Living Radical Polymerization. *Macromolecules* 2000, 33, (18), 6732-6737.

We turn now to the third embodiment.

A feature of this embodiment is a composition containing the NOHMs of the first embodiment. The NOHMs are present in the composition alone or in combination with other components. In other words, there are applications for these NOHMs, where no additional components are needed. For example, as discussed in more detail below, NOHMs have been developed by the inventors of the present application that can be used as a lubricant without having to add any additional components.

In another feature of this embodiment, at least two different NOHMs are combined to form a composition. The at least two different NOHMs have different organic polymeric coronas and/or inorganic nanoparticle cores. For example, a first NOHM contains an organic polymeric corona that is different from the second NOHM. The organic polymeric corona of the first NOHM is preferably is selected from the group consisting of EVA, PVC, PEG, PEO, POE, PDMS, PAO, and PVDF and the organic polymeric corona of the second NOHM is selected from the group consisting of EVA, PVC, PEG, PEO, POE, PDMS, PAO, and PVDF. Despite each NOHM having a different organic polymeric corona, the NOHMs are miscible and the composition exhibits liquid-like properties so that the NOHMs move freely and flow in a manner so that when the NOHMs are in a container, the NOHMs take the shape of the container. The addition of a suspending solvent is optional.

NOHMs exhibit features of synthetic polymers (e.g. low density, low cost, and facile low-temperature processing), along with unusual functionalities (e.g. mechanical strength, high refractive index, lithium ion intercalation, thermal/electrical conductivity, photovoltaic properties) typical of inorganic materials.

In this regard, NOHMs are useful for a wide range of applications, such as lubricants, personal care products (e.g. sunscreens), adhesives formulations, ferrofluids, paints, coatings, LIB electrodes, electrolytes for rechargeable batteries, electrolytes for fuel cells, shear-thickening coatings, and adhesive formulations. For example, the addition of NOHMs to a composition is desirable, wherein the covalent attachment of the suspending media to particle cores reinforces the mechanical properties of the polymer corona; and suggests that the vapor pressures of the liquids are low, facilitating high temperature operations without the need for expensive packaging/sealing.

In yet another aspect of this invention, NOHMs are able to behave as a fluid in part because the effective solvent (e.g., organic polymeric corona) is chemically tethered to the inorganic nanoparticle core. As a result, the vapor pressures of NOHMs liquids tend to be negligible.

This feature generally makes NOHMS suitable for high temperature applications (e.g. as lubricants, heat transfer liquids for solar thermal cells, and rechargeable battery electrolytes/electrodes), where colloidal suspensions either cannot be used or require specialized packaging designs to inhibit solvent loss. A high temperature application is an application that utilizes temperatures from 250 to 600° F., and preferably 300 to 500° F.

In one aspect of this embodiment, NOHMs are produced that exhibit large ion mobilities and high mechanical moduli (e.g., NOHMs as an electrolyte); low viscosity and high thermal conductivity (e.g., NOHMs as a lubricant); high moduli and shear thickening rheology (e.g., NOHMs as a coatings and stable liquid body armor); phase change capability and high heat transfer (e.g., NOHMs as an electrolyte). These properties are obtained by manipulating/varying the geometric and steric characteristics of the inorganic core particle and organic polymeric corona.

A preferred feature is that the NOHMs of the invention can be used to produce an electrolyte in light of the remarks that follow. Reliable, cost-effective technologies for efficiently storing and retrieving electric power have long been recognized as the limiting factor in portable technology development. Currently, rechargeable batteries are the technology of choice, but even the best systems are expensive, accident-prone, cumbersome, and suffer from gradual loss of capacity over time; there exists a need for a safe, reliable battery with higher energy density and sufficient recharge rates. Lithium is the lightest and most electropositive metal, thus rechargeable batteries based on lithium anodes offer the potential for exceptional energy storage capabilities in a light-weight platform (see Linden, D.; Reddy, T. B. *Handbook of Batteries*, $3^{rd}$ Ed., McGraw-Hill, New York (1995)). Lithium is also more abundant and cheaper than Ni—its primary competitor for high energy density rechargeable batteries. Rechargeable lithium metal batteries generally suffer from two main problems that mitigate the advantages outlined in the previous section. First, electrochemically-induced lithium dendrite growth during charge/discharge cycles produces internal short circuits, which are a fire/explosion hazard. Second, lithium metal dendrites generated over multiple charge/discharge cycles form a high surface area mossy film at the lithium anode that reacts with many electrolytes to deplete lithium metal from the battery. Prior to the present invention, a common solution was to use a three- to four-fold excess of lithium metal in the anode to minimize loss of storage capacity (fading) over time (see Linden, D.; Reddy, T. B. *Handbook of Batteries*, $3^{rd}$ Ed., McGraw-Hill, New York (1995)).

Another solution was to also use solid polyethylene oxide (PEO/PEG) electrolytes. Lithium metal reacts minimally with PEO/PEG, so that capacity fading is also avoided in lithium batteries employing solid polymer electrolytes. A draw-back of based on solid polymer electrolytes, however, is that the internal resistance is high at normal operating temperatures. A direct consequence is that the discharge rate of lithium polymer batteries are as a rule low (i.e. a 2-3× oversized battery is required to deliver the power needed for fast acceleration in electric vehicles). The battery also had to be operated at elevated temperatures to achieve sufficient current flow. It is not unusual for these types of batteries to have to operate at temperatures above the melting point of the solid electrolytes (e.g., above 60° C. for PEO/PEG electrolytes). Both deficiencies of lithium polymer batteries can be easily traced to the low ionic conductivity of the solid electrolyte.

The NOHMs of the first embodiment can be used as conductive liquid electrolytes that are un-reactive with lithium, possess high ionic conductivities at ambient temperatures, and provide a complex pathway that can be used to dramatically slow-down/eliminate dendrite growth between battery electrodes. Specifically, because the volume fraction of inorganic nanoparticle cores in the NOHMs is high, dendrites may only grow in the confined pathways offered by the organic polymeric corona chains. Because the organic polymer corona chains are short and their coverage on the cores high, transport of lithium ions will be unaffected, leading to high ionic conductivities.

In one aspect of this invention, the NOHMS are doped with a lithium salt selected from the group consisting of $LiCF_3SO_3$, $LiN(CF_3SO_2)_2$, $LiC(CF_3SO_2)_3$, $LiC(CH_3)(CF_3SO_2)_2$, $LiCH(CF_3SO_2)_2$, $LiCH_2(CF_3SO_2)$, $LiC_2F_5SO_3$, LiN(C$_2$F$_5$SO$_2$)$_2$, LiB(CF$_3$SO$_2$)$_2$, LiPF$_6$, LiClO$_4$, LiI, LiBF$_4$, LiSCN, LiAsF$_6$, NaCF$_3$SO$_3$, NaPF$_6$, NaClO$_4$, NaI, NaBF$_4$, NaAsF$_6$, KCF$_3$SO$_3$, KPF$_6$, KI, LiCF$_3$CO$_3$, NaClO$_3$, NaSCN, KBF$_4$, Mg(ClO$_4$)$_2$, and Mg(BF$_4$)$_2$. The NOHMS are preferably doped with LiClO$_4$, LiPF$_6$, LiCF$_3$SO$_3$, LiAsF$_6$, or LiN(CF$_3$SO$_2$)$_2$ and the inorganic nanoparticle cores are preferably selected from the group consisting of TiO$_2$, SiO$_2$, SnO$_2$, Fe$_2$O$_3$, Fe$_3$O$_4$, and CO$_3$O$_4$ The electrolytes can be formed via two routes: sulfonic acid functionalization of the silica nanoparticle suspension followed by reaction with an amine terminated polyethylene glycol methyl ether as set forth in scheme 2 (see pathways 1 and 2) and direct reaction of a trimethoxysilane functionalized polyethylene glycol methyl ether with nanoparticle suspensions of either silica or titania (see pathway 3).

Scheme 2 is as follows:

FIG. 1 further shows that ionic conductivities of the SiO$_2$-PEG NOHMs electrolytes can exceed those of solid-PEO electrolyte by amounts ranging from 1 to nearly 5 orders of magnitude, depending on the temperature. The fact that these large improvements in ionic conductivity are achieved in materials with comparable or better thermal, mechanical, and viscous properties evidences that electrolytes comprising NOHMs of the first embodiment exhibit a number of desirable properties. It is also noteworthy that NOHMs electrolytes represented by the filled triangles in FIG. 1 are large enough that these materials manifest a yield stress. This means that at low stresses they will resist deformation in an analogous manner to a solid. At higher stresses they flow like liquids. Together these features mean

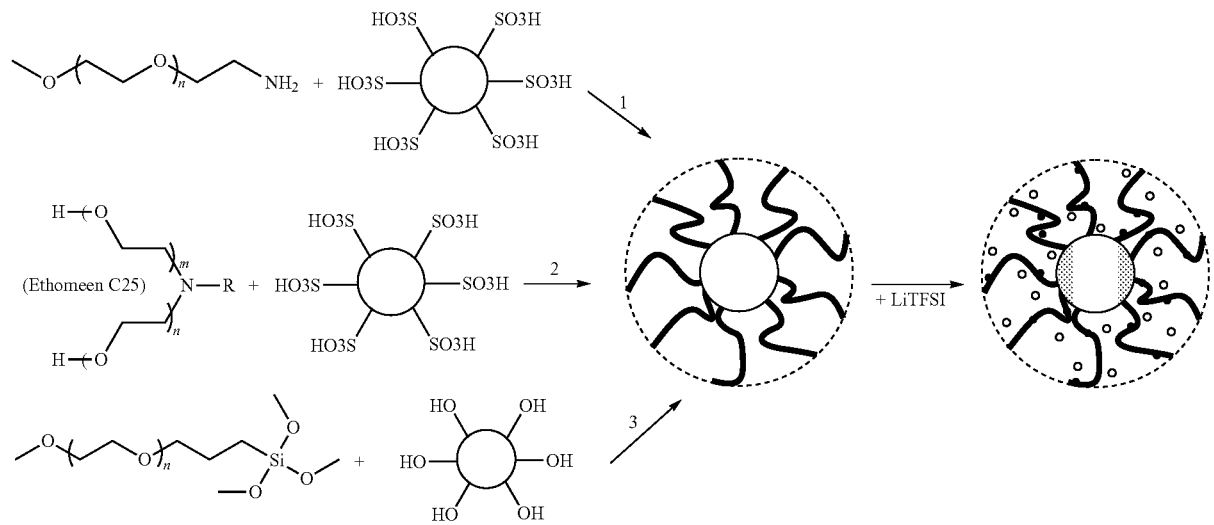

After synthesis, the hybrids are mixed with a lithium salt to form an electrolyte of lithium salt (e.g., 1M-3M) in the organic phase. Both synthetic routes yielded electrolytes with uniformly disperse nanoparticle cores.

NOHMs constructed from hard inorganic particles and corona with good lithium ion conductivities (e.g. LiClO$_4$, LiPF$_6$, LiCF$_3$SO$_3$, LiAsF$_6$, or LiN(CF$_3$SO$_2$)$_2$-doped PEG oligomers with M$_w$<10000 g/mol), novel room-temperature liquid electrolytes capable of arresting harmful dendrite growth in rechargeable lithium metal batteries can be created. Additional control over NOHMs physical properties can be achieved by exploiting a large library of available inorganic particle chemistries and shapes (liquid NOHMs based on SiO$_2$, SnO$_2$, γ-Fe$_2$O$_3$, Fe$_3$O$_4$, and CO$_3$O$_4$ nanocores have already been demonstrated).

FIG. 1 is an Arrehenius temperature plot summarizing ionic conductivities of SiO$_2$—PEG NOHMs (symbols) with varying core particle volume fractions (fc). Conductivities for currently used solid-PEO electrolytes (broken line) and the untethered PEG corona used to create a NOHM electrolyte are presented for comparison. LiClO$_4$ salt is used as the ionic dopant. It is evident from FIG. 1 that the ionic conductivities for these PEG-based NOHMs are only weakly dependent on the temperature and volume fraction of the NOHMs. FIG. 1 also shows that the ionic conductivities of the NOHMs liquids are generally comparable to those of the oligomeric PEG corona (continuous line) over the entire range of temperatures studied.

that by varying the fc of the NOHMs, an electrolyte is obtained that is capable of inhibiting arrest growth of lithium dendrites Based on rheological and ionic conductivity measurements employing NOHMs with a range of fc values, NOHMs employing a lithium ion conducting polymer, e.g. PEG or PVDF, are preferred for use as electrolytes. NOHMs having a fc in the range 0.1≤fc<0.5 are also preferred. Thus, an aspect of this embodiment is a functional room-temperature electrolyte (i.e. ionic conductivity>10$^{-4}$ S/cm at 25° C.). In NOHMs having a fc less than 0.1, the mechanical properties of these materials do not limit dendrite growth as well. Likewise, while it is possible to create NOHMs having fc>0.5, which can completely localize dendrites to the region around the Li anode, the conductivity of these materials are not as desirable.

The preferred overall volume fraction of the inorganic nanoparticle cores (i.e. based on the volume of the inorganic nanoparticle core relative to corona and plasticizing electrolytes) of NOHMs is also in a range of about 0.1 to about 0.5, where both the conductivities and mechanical properties of the electrolytes are suitable for lithium battery applications.

A feature of this embodiment is a rechargeable battery, comprising: (i) an electrolyte as discussed above, (ii) a lithium metal anode, and (iii) a cathode (see Xu, onaqueous Liquid Electrolytes for Lithium-based Reachargeable Batteries, *Chem Review,* 104, 4303-4417 (2004), the entirety of which is incorporated by reference). A separator is not required.

Another feature of this embodiment is that the NOHMs of the first embodiment can be used alone or in combination with other components as a lubricant. Lubricants with dielectric properties that match those of the components they lubricate, and which possess high mechanical moduli and good thermal conductivity are often needed to operate high-performance machinery and aircraft. Prior to the present invention, these requirements have been met by dispersing conducting particles such as $SiO_2$, $TiO_2$, $Al_2O_3$, $Fe_3O_4$, Ag, Cu, or graphite, in organic lubricating oils and greases. The introduction of nanometer sized particles has also been attempted, but aggregation between the surface-area particles has limited use of these materials.

A lubricant comprising NOHMs of the first embodiment overcomes these deficiencies. In particular, by varying the architecture of the organic polymeric corona and/or inorganic polymeric core of the NOHM, the properties of the lubricant can be varied. For example, the molecular weight of PEG-ethoxy silane corona chains of the NOHMs. For PEGs with molecular weights below 2,500 g/mol, the viscosity of the lubricant becomes lower as the corona polymer molecular weight is increased. The organic polymeric corona can also be functionalized to manipulate the properties of the NOHMs and lubricant. For example, the hydroxyl group at the end of PEG-based NOHMs provides a route for introducing a host of functionalities to the NOHMs corona—by covalent attachment.

The size of the inorganic nanoparticle varies. For example, up to a five-fold increase in viscosity can be observed when the core particle diameter is increased from 15 nm to 30 nm, keeping the corona polymer molecular weight and surface grafting density fixed. Addition of non reactive PEG (e.g. PEG-dimethyl ether) provides another effective means for manipulating the flow properties of the NOHMs, along with the lubricant.

Moreover, if a higher thermal conductivity is desired, the NOHMs can be produced with metal inorganic nanopartcles. The synthesis of NOHMs based on metallic cores is achieved by straightforward extension of the organic polymeric coronas as discussed earlier. Specifically, if a metal (e.g Au or Pd) inorganic nanoparticle core is desired, an oligomer polymers bearing thiol or amine groups at one end can be employed to couple via a hydrogen bond or covalent bond the organic polymers to the inorganic nanoparticle cores.

If other conducting metals (e.g. Cu, Ag, or Pb) inorganic nanoparticle cores are desired, organic polymeric corona bearing different kinds of function groups of carboxylic acid, sulfonic acid, or the corresponding acid chlorides or anhydrides must be used.

In one feature of this embodiment, the lubricant has a velocity independent fraction coefficient of 0.1 to $6 \times 10^{-3}$ and preferably 0.1 to $4 \times 10^{-3}$, and more preferably at 1 to $4 \times 10^{-3}$ at room temperature.

In yet another aspect of this embodiment, a shear thickening material is obtained by adding cube-shaped $CO_3O_4$ nanoparticles to a cream, coating, or gel. A benefit of cube-shaped NOHMs is that these materials manifest desirable shear-thickening features at moderate shear rates, which can be employed as the basis for novel protective creams and gels for law enforcement and military personnel.

Example 1

$SiO_2$—PEG NOHMs are produced by adding 700 ml of reverse osmosis (RO) water to a 1 L glass bottle with magnetic stirrer rotated at high speed>500 rpm; slowly adding a 333 g Ludox AS-30, TM-30, or SM-30 aqueous suspension (i.e. 100 g $SiO_2$) to the water and then stirring; dissolving 100 g PEG-ethoxysilane in 200 ml water; vigorous stirring; continue stirring for 10 hours with intermediate conditions at 12 hours at 110° C.; transferring the resulting material to an evaporating dish (glass); and placing the resulting material and dish in a convection oven at 75° C. until water has evaporated.

The resultant materials show that as the volume fraction of the $SiO_2$ core particles is decreased from fc≈0.55, to 0.34 to 0.23 the consistency of the nanoparticle organic hybrid materials (NOHMs) changes from a non-flowing gel, to a simple viscous liquid.

Example 2

NOHMs produced using the procedure described in Example 1 are re-suspended in water and any un-tethered corona chains are removed by dialysis. In the dialysis approach, the re-dissolved material is added to the interior of a Spectrum laboratories dialysis bag (5 nm. size cut-off). The end is closed with tubing clamps. The material to be dialyzed is submerged in a 1000 ml bath containing RO water and dialysis allowed to proceed with gentle stirring. For the first 12 hours of dialysis, the water in the bath was refreshed every four hours. For the remaining 12 hours, the water was refreshed once.

Thermal gravimetric analysis (TGA) was used to characterize the organic content of the materials obtained after the dialysis procedure. Results indicate that approximately 32% of the mass of each hybrid nanoparticle consists of PEG. The PEG has a molecular weight ($M_w$) of 550 g/mol and an inorganic particle core having a diameter of nm. This implies that there are on average 650 PEG chains tethered to each silica inorganic nanoparticle core.

Example 3

Biodegradable NOHMs are produced by adding 700 ml of reverse osmosis (RO) water to a 1 L glass bottle with magnetic stirrer>500 rpm; adding a NaOH base to adjust the pH of the water to 9-10; slowly adding 333 g Ludox AS-30, TM-30, or SM-30 aqueous suspension to the water (i.e. 100 g $SiO_2$) and then stirring to form a solution; dissolving 100 g of PEG-ethoxysilane in 200 ml water to form a mixture; and slowly adding the solution and mixture together with stirring; stirring for 1 hour at 100° C. with intermediate periods of ultrasonification; transferring the material to an evaporating dish (glass); and placing dish and material in a convection oven at 75° C. until water is removed after 12 hours.

The product of this synthesis is labeled S1.

The hydroxyl group at the end of the S1-series PEG-based NOHMs provides a route for introducing a host of functionalities to the NOHMs corona—by covalent attachment. We reacted the S1 NOHMs with a 2:1 molar excess (i.e. based on the mole fraction of terminal hydroxyl groups on the PEG) of epichlorohydrin in dichloromethane or THF (i.e., 100 g S1 NOHMs, 15 g epichlorohydrin, 2 g sodium hydroxide pellets, and 100 ml dichloromethane/THF). The reactants were reacted for 24 hours under an aqueous solution reflux. This reaction transforms terminal hydroxyl groups on the PEG to epoxide groups. The resultant epoxy functionalized PEG was separated from the unreacted epichlorohydrin and sodium hydroxide by centrifugation and repeated washing with solvent.

The epoxy functionalized S1 material was dispersed in dichloro methane and an equimolar (again based on the amount of reactive terminal groups in a 100 g sample) and amine terminated polydimethylsiloxane (PDMS, silicone oils) were added to the mixture. Upon addition of 2 grams of $SnCl_2$ catalyst, the amine-epoxy reaction was allowed to proceed to completion (24 hours under reflux with vigorous stirring).

Figure 2:
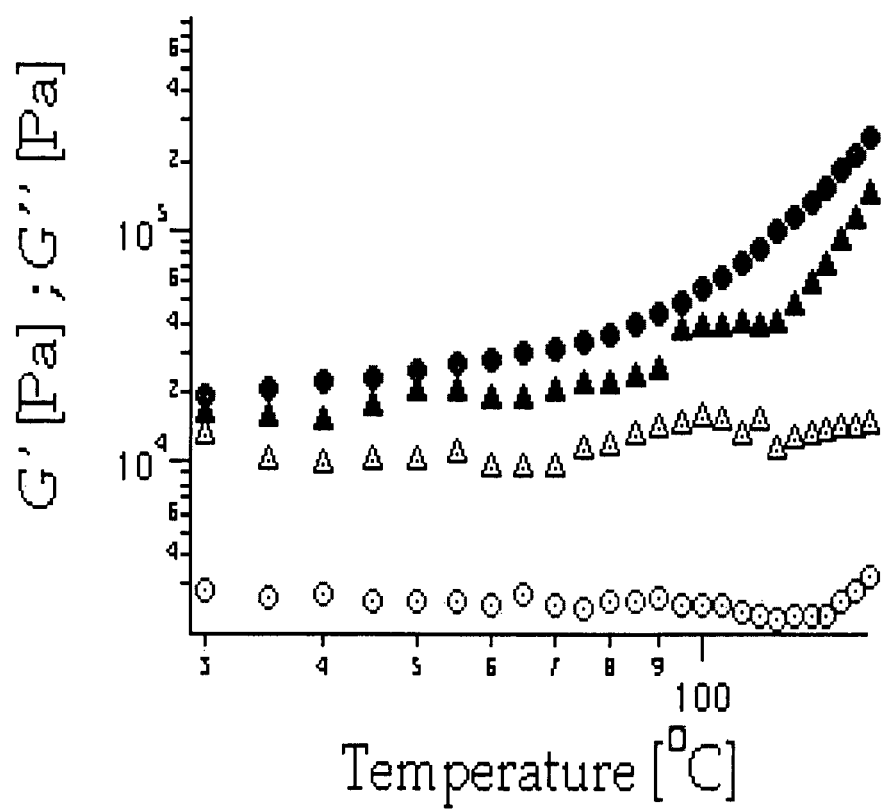
FIG. 2 shows Storage and Loss Modulus of NOHMs as function of temperature, $\omega=10$ s$^{-1}$, and strain=1%.

Residual $SnCl_2$ was removed by filtration and repeated washing with THF. The material was transferred to an evaporating dish and the solvent removed by evaporation in a convection oven maintained at 80° C. for 8 hours. The material is labeled S2 material. The triangles in FIG. 2 illustrate how the storage and loss moduli for this material varies with temperature. It is apparent from this figure, that the S2 material has a lower viscosity than its S1 precursor, but the viscosity is less temperature dependent.

Equimolar amounts of 2 M solutions of steric acid and octadecanoic acid, respectively, in warm organophilic solvents (e.g. dichloro methane or chloroform) were added to another portion of the S1 material in the same solvent discussed above. The reaction was allowed to proceed under reflux with vigorous stirring for 24 hours, to produce a hydrophobic (steryl or octadecanyl) canopy on the exterior of a PEG corona. The materials were labeled S3 and S4, respectively. In comparison to the corona, the canopy molar mass is small, which means that the overall volume fraction of the cores in the S3 and S4 is only marginally different from the S1 material. This treatment nonetheless results in a greasy/waxy material. The organophilic canopy tethered to the PEG corona also makes the NOHMs amphiphilic.

FIG. 2 summarizes the corresponding mechanical properties of the S1 series NOHMs. Specifically, this figure plots the elastic or storage modulus, G', (filled symbols) and the viscous or loss modulus, G", (open symbols) as a function of temperature. Circles are data for the S1 series material represented by the continuous line (ie. containing approx 40 wt % silica, $\omega_{SiO2} \approx 0.4$). The triangles are data for the S2 material ($\omega_{SiO2} \approx 0.2$). The materials manifest solid-like (G'>G") mechanical response and that they maintain high viscosities over the full range of temperatures (30° C.-150° C.) studied.

Example 4

Amine-based NOHMs are produced by adding 700 ml of Reverse Osmosis (RO) water to a 1 L glass bottle with magnetic stirrer>500 rpm; adding KOH in dry or aqueous form to adjust the pH of the water to 9-10; slowly adding 333 g Ludox AS-30 suspension of silica nanoparticles in water (i.e. 100 g $SiO_2$) to the water to form a mixture; dissolving 100 g of (3 Trimethoxysilylpropyl) diethylene triamine (TMPDT) in 200 ml water to form a solution; slowly adding the solution and mixture, with vigorous stirring together; stirring for 10 hours at 120° C. with 20 minute periods of ultrasonication every fours; allowing approx ¾ of the volume of water to evaporate. The solution maintains a uniform, pale yellow appearance and has a consistency similar to that of water. The material is then transferred to an ultracentrifuge and centrifuged for 2 hours at 40 k rpm. The supernatant is decanted and redispersed in RO water. This procedure was repeated three times to remove unattached TMPDT and base. The product was then washed in THF. 100 g of the material was then dispersed in 500 ml of dichloromethane. An equimolar amount (based on TGA analysis of solid product produced by drying the suspension, which indicates that there are approx 2.5 TMPDT molecules per $nm^2$ of surface area of silica), of a commercial monofunctional, epoxy terminated, PDMS (Aldrich, $M_w$, PDMS=5,000 g/mol) and 5 grams of a $SnCl_2$ catalyst is added to the mixture. The resulting reaction is allowed to proceed for at least two days at room temperature with vigorous stirring. The resulting product is washed with water to remove the $SnCl_2$ catalyst and dried dry overnight in a convection oven to recover the PDMS NOHMs.

Example 5

Sixty grams of $NaNO_3$ was added to a 3 neck flask with a condenser attached. Thirty milliliters of 1M NaOH and 70 mL of deionized water were subsequently added to the flask. The flask was placed in a silicon oil bath set to a temperature of 120° C. A continuous supply of air at 50 ml/min was bubbled into the system. Twenty milliliters of 1M $Co(NO_3)_2$ was added drop wise to the flask after the temperature in the flask had equilibrated. This synthesis was allowed to proceed for 22 hours and yielded a black suspension.

After allowing 5 minutes for cooling, 100 mL of 0.1M of HCl was added to the contents of the flask and the mixture maintained at room temperature for 24 hours to allow solid side products produced in the synthesis to be dissolved and separated from the targeted product, $CO_3O_4$ nanocubes. The supernatant was discarded and the bottom phase centrifuged at 6000 rpm for 30 minutes to further separate the by products. This procedure was repeated three times to enhance the purity of the $CO_3O_4$ product. Glycerol was added to the bottom phase and thoroughly mixed into the particles.

The same procedure was employed for tethering PEG to the surface of silica in Example 2 was used to covalently attached PEG chains with molecular weights ranging from 500 g/mol to 10 kg/mol to the surface of the $CO_3O_4$ cubes. For PEG molecular weights below 1.5 kg/mol, the resulting $CO_3O_4$ NOHMs were neat black liquids. For higher PEG molecular weights, the NOHMs though solid at room temperature, manifest a dramatic melting transition at a temperature close to 60° C., the melting temperature of PEG.

The viscosity of the $CO_3O_4$ NOHMs at 65° C. for systems where the volume fraction fc of the cores ranges from 0.36 to 0.62. In addition to the usual shear-thinning characteristics (viscosity reduces with increasing shear rate), the NOHMs liquids manifest a regime at high shear rates where the viscosity increases with shear rate.

The shear-thickening transition in suspensions of spheres is generally attributed to formation of hydroclusters at a critical Peclet number, $Pe_c \equiv \dot{\gamma}^* * \eta_s/(kT/d^3)$, of order unity; here $\dot{\gamma}$ is the shear rate, d the particle dimension, $\eta_s$ the suspending medium viscosity, k Boltzmann's constant and T the Kelvin temperature. $Pe_c=0.07$ for fc=0.62, and that the magnitude of the viscosity rise is generally larger. Applicants do not want to be bound by any particular theory but it is believed that shear-induced formation of hydroclusters is resisted by large forces needed to confine the captive solvent—i.e., the tethered corona.

Example 6

NOHMs were produced with PEG corona ranging from 500 to 5000 molecular weight; inorganic fractions ranged from 12 to 49 wt %. Table 1 displays the specifications for these electrolytes. The NOHMs were then doped with LiTFSI as follows:

TABLE 1

NOHMs Electrolyte Specifications

| Elect. # | Synthesis Pathway in FIG. 1 | Core Chemistry | Core Diameter (nm) | PEG Corona MMW (g/mol) | Core Fraction | Cryst. Temp., $T_c$ (° C.) | Melting Temp., $T_m$ (° C.) |
|---|---|---|---|---|---|---|---|
| 1 | 1 | $SiO_2$ | 8 | 550 | 0.48 | −36 | 10 |
| 2 | 3 | $SiO_2$ | 8 | 595-725 | 0.45 | −39 | 5 |
| 3 | 1 | $SiO_2$ | 8 | 800 | 0.40 | −35 | 10 |
| 4 | 2 | $SiO_2$ | 8 | 825-909* | 0.43 | — | |
| 5 | 1 | $SiO_2$ | 8 | 1100 | 0.36 | | |
| 6 | 1 | $SiO_2$ | 8 | 2000 | 0.24 | −12 | 31 |
| 7 | 1 | $SiO_2$ | 8 | 5000 | 0.12 | 23 | 44 |
| 8 | 3 | $SiO_2$ | 18 | 595-725 | 0.49 | −35 | 5 |
| 9 | 3 | $TiO_2$ | 15 | 595-725 | 0.39 | −30 | 9 |

*Full molecular weight of branched poly(ethylene glycol) functionalized amine (Ethomeen C25)

The thermal properties of the hybrid electrolytes were measured by differential scanning calorimetry (DSC) and thermal gravimetric analysis (TGA). The inorganic nanoparticle fraction of each hybrid, prior to the addition of LiTFSI, was determined by TGA as reported in Table 1. The electrolytes were thermally stable to near 300 deg C. Samples #6 and #7 that displayed melting transitions above room temperature by DSC were those with the longest corona, 2000 and 5000 molecular weight; these electrolytes are soft, semi-crystalline, self-supporting gels at room temperature.

Figure 3:
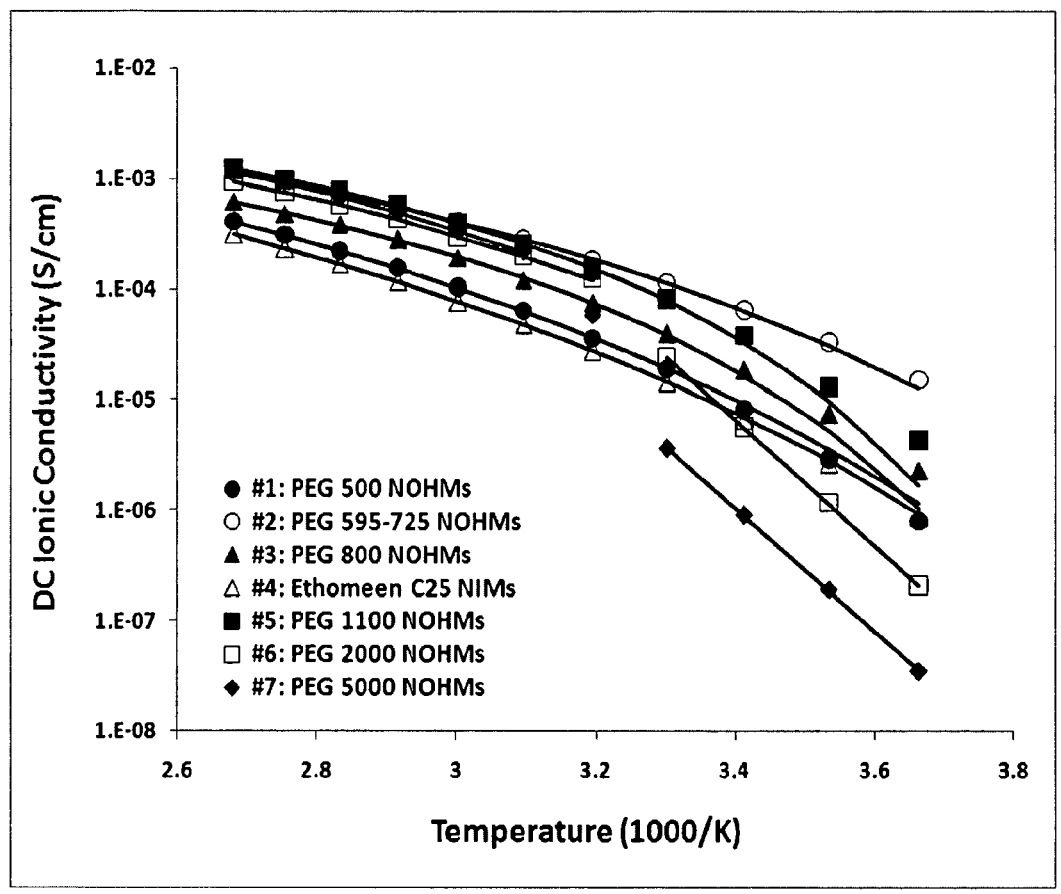
FIG. 3 shows results of a DC ionic conductivity of NOHMs electrolytes with 8 nm SiO$_2$ cores and varying types of PEG corona.
Figure 4:
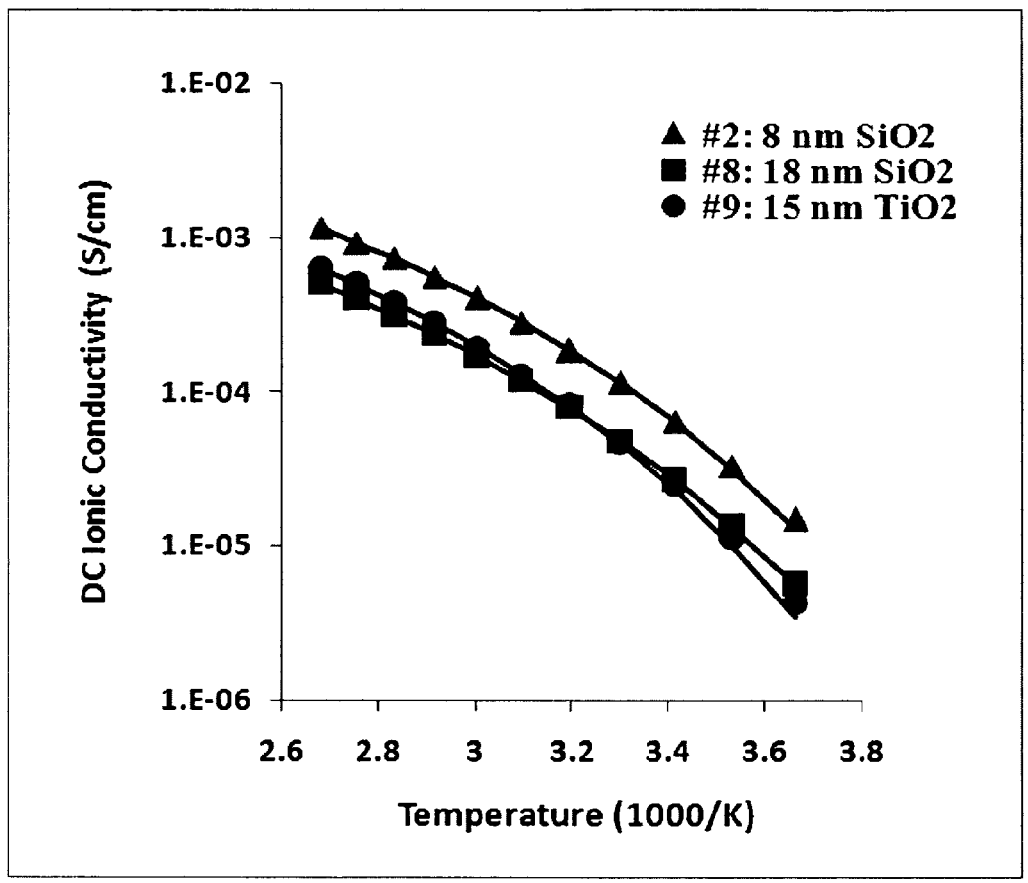
FIG. 4 shows the DC conductivity of NOHMs electrolytes with varying inorganic nanoparticle core chemistry and size.

The dielectric properties of the electrolytes were studied using temperature dependent broadband dielectric spectroscopy. DC ionic conductivity values as well as the frequency of tan(δ) maxima were extracted from this data. FIG. 3 displays temperature dependent ionic conductivity data for hybrids with 8 nm silica cores and varying length polyethylene glycol corona, electrolytes #1-7. FIG. 4 displays conductivity of hybrids with varying core sizes and chemistry, all with 595-725 molecular weight PEG corona, electrolytes #2, 8-9. The lines on FIGS. 3 and 4 are fits to Vogel-Thamman-Fulcher (VTF) or Arrhenius temperature dependence.

FIG. 3 shows that PEG corona length has a large effect on ionic conductivity, especially at ambient conditions. Electrolytes #6 and #7 that exhibit both a crystalline and melt transition accessible during the temperature dependent dielectric measurements have an Arrhenius temperature dependent ionic conductivity below the melt transition. All other samples exhibited VTF conductivity throughout, which indicates that the conduction mechanism is governed by the segmental motion of the oligomer chains. In addition, the frequency maximum of the tan(δ) as extracted from the dielectric data exhibits analogous temperature dependence as with the conductivity, with activation and pseudo-activation energies within error of that of the ionic conductivity. The mechanism for ion transport is coupled to the relaxation of the tethered oligomer chains. Several of the hybrids reach the same conductivity, within error, at high temperatures; this conductivity is similar to that recorded for a pure high molecular weight PEO-LiTFSI system. Thus, the PEG chains in these systems have similar dynamics at the microscale. Hybrids with short corona (#1, #3, #4) have poor conductivity in comparison with the other systems, this is likely due to slower relaxation as a result of chain tethering. The sample with the highest ionic conductivity at room temperature, electrolyte #2, has a polydisperse corona.

FIG. 4 shows an increase in the hybrid core size, even while maintaining organic fraction, results in a fractional decrease in ionic conductivity. This could be due to decreased segmental motion in the matrix as a result of increased chain crowding and extension around the cores. The change in core chemistry from silica to titania appears to have a negligible effect on ionic conductivity. This further implies that the mechanism of ion transport is through motion of the PEG chains and that the inorganic cores have little effect on the transport pathway.

Figure 5:
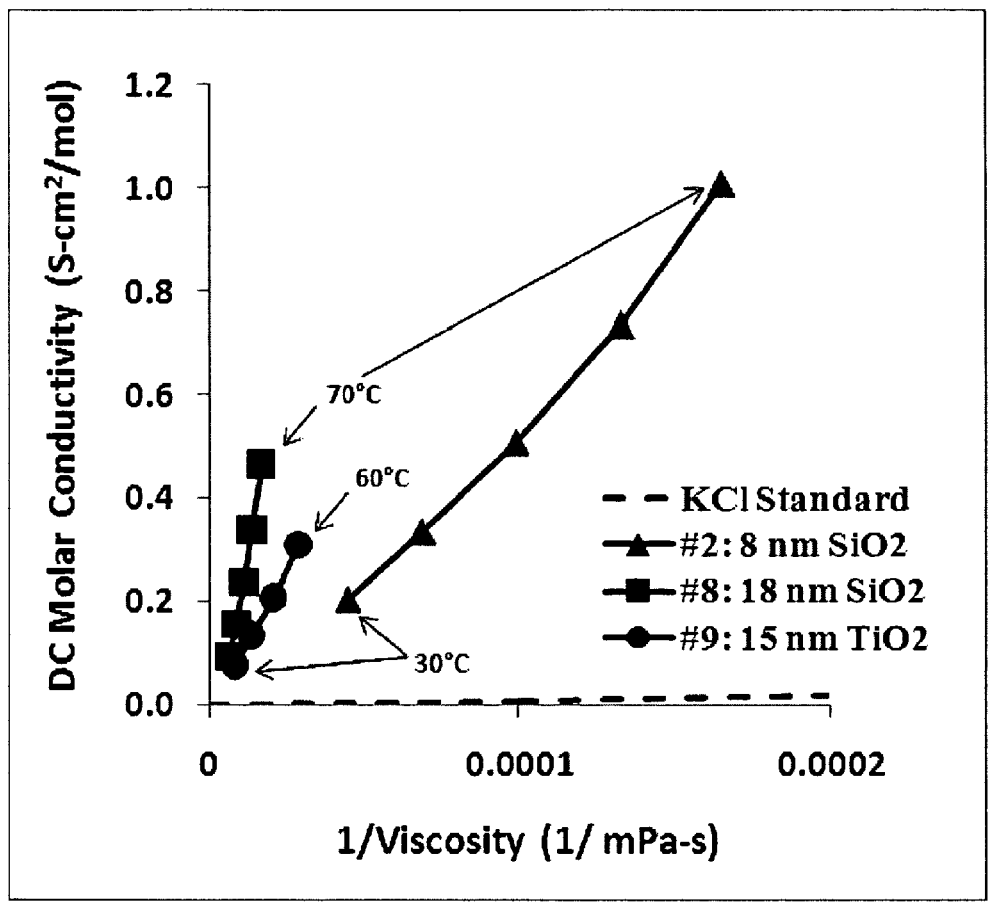
FIG. 5 is a Walden plot of NOHMs electrolytes with varying inorganic nanoparticle cores and 595-725 PEG corona.

FIG. 5 displays the DC molar conductivity vs. the shear fluidity (inverse viscosity), the Walden plot of the same electrolyte series (#2, #8, #9) with varying cores and 595-725 molecular weight PEG corona. Compare FIG. 5 with FIG. 6, the Walden plot of polyethylene glycol monomethyl ether (MPEG) oligomers doped with 1 M LiTFSI. In both plots, the dashed line represents the standard result for dilute KCl in aqueous solution. The data for the NOHM electrolytes in FIG. 5 is presented from 30-70° C.; the data for MPEG electrolytes in FIG. 6 is presented from 70-100° C. as several samples were crystalline at room temperature.

FIG. 5 illustrates that the NOHMs electrolytes even with short PEG corona are superionic according to Walden plot standards: high ionic conductivity relative to fluidity. In comparison, free MPEG electrolytes are superionic only in the entanglement regime (MW>3200), as shown by FIG. 6. Moreover, the superionic regime is accessible at room temperature with NOHMs electrolytes. The Walden plot has not commonly been used in the display of polymer electrolyte data, as the traditional use of the plot was to understand the microscopic behavior of ions moving in small molecule solvent and a macroscopic property; the standard KCl data is of a dilute, fully dissociated solution of ions of equal mobility. While the conduction mechanism in polymer electrolytes is more closely related to free volume than viscosity, the Walden plot does show that the electrolytes exhibit good conductivity and viscosity.

Figure 6:
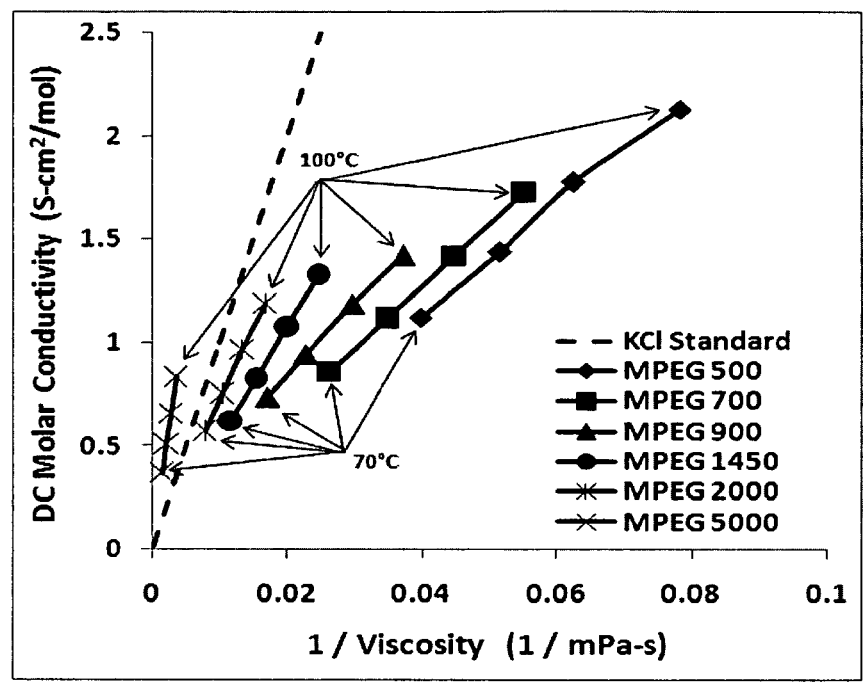
FIG. 6 is a Walden plot of MPEG electrolytes.
Figure 7:
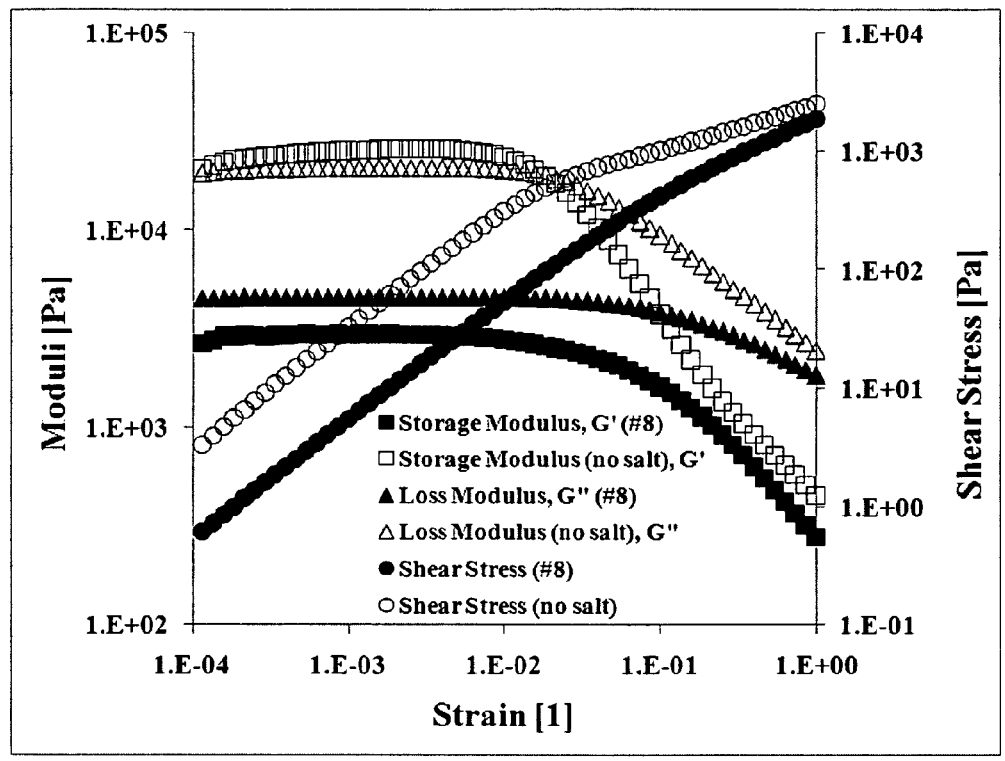
FIG. 7 shows the shear stress, storage, and loss modulus of a NOHMs electrolyte (filled symbols) and NOHMs without LiTFSI (open symbols) undergoing a strain sweep with $\omega=10$ rad/sec.

Comparison of FIGS. 5 and 6 also shows that while MPEG electrolytes have a linear relationship between conductivity and fluidity, this relationship is non-linear for NOHM electrolytes. This is because while MPEG conductivity and fluidity as well as NOHM conductivity above the melt transition has VFT temperature dependence, the NOHM electrolyte shear fluidity has Arrhenian temperature dependence. It is also apparent from FIG. 5 that the change in core size has a greater effect on viscosity than conductivity; an increase in core diameter from 8 to 18 nm increases viscosity by nearly an order of magnitude, whereas conductivity decreases only fractionally. This behavior is consistent with jamming of the hybrid cores during shear flow. This finding is in agreement with results from strain sweep measurements (FIG. 7), which show a well-defined yield stress for both the salt-free and LiTFSI-doped NOHMs. The yielding transition is accompanied by strain softening moduli, and for the salt-free NOHMS, a weak maximum in G", indicative of soft-glassy rheology. It is therefore clear that addition of LiTFSI to the hybrid results in a significant decrease in the moduli. This result has been noted for other PEO-LiTFSI systems, typically attributed to a drop in the crystalline fraction of PEO, as discussed by Edman, L., Ferry, A. & Doeff, M. M., Slow recrystallization in the polymer electrolyte system poly(ethylene oxide)n-LiN(CF2SO2)s. Journal of Materials Research 15, 1950-1954 (2000).

Example 7

Hydroxy(polyethylyeneoxy)propyl]triethoxysilane, 50% in ethanol (SIH6188.0, silane-PEO, PEO MW between 500 and 550) was used as received from Gelest, Inc. Water, potassium hydroxide (KOH), and silicon dioxide nanoparticles (Ludox SM-30, 30% in water) were used as received from Sigma-Aldrich. Ludox solution was diluted to 4% (w/v) with a KOH solution of pH 10. The silane-PEO solution was added dropwise while stirring to the diluted Ludox solution to inhibit aggregation of the silicon dioxide nanoparticles. This Ludox-silane-PEO solution was placed, uncapped in a 100° C. oil bath for 1 hour. The solution was ultrasonicated for 15 minutes and returned to the 100° C. oil bath for 1 hour. The solution was ultrasonicated for another 15 minutes and returned to the oil bath for 6 hours. The ultrasonication was performed to inhibit aggregation of the nanoparticles and promote even graft density of the silane-PEO to the nanoparticles. The resulting solution was put in a large petri dish and placed in a convection oven, uncovered, at 70° C. until all of the water had evaporated. The nanoparticle-silane-PEO was collected from the petri dish and stored in a 100 mL media bottle in a glovebox under argon. The synthesis of an inorganic nanoparticle-tethered initiator is illustrated by scheme 3 as follows:

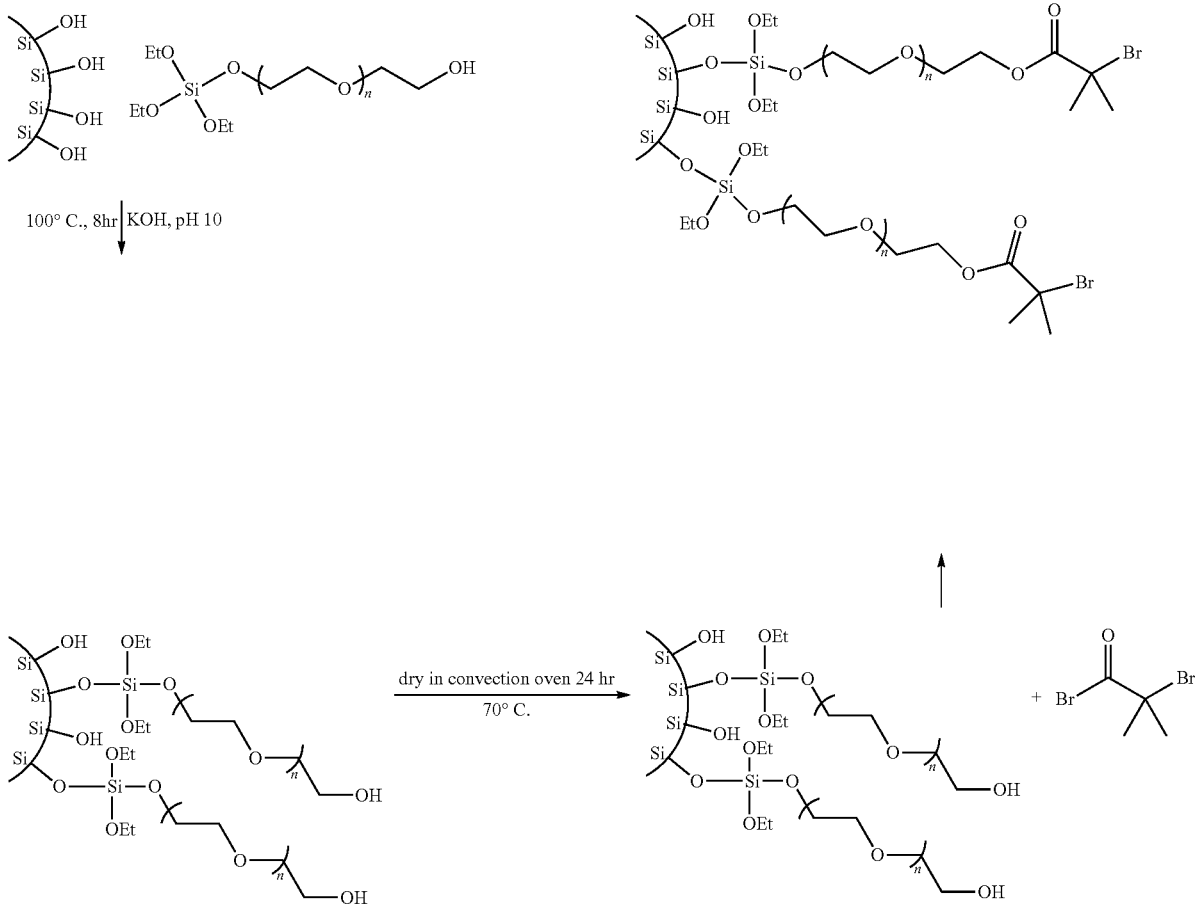

Tetrahydrofuran (THF) was purified in a solvent still under nitrogen using 1,1-diphenylethylene 97% and n-butyllithium. 1,1-diphenylethylene was added in a ratio of 1 drop to 50 mL THF. n-butyllithium was added in a ratio of 1 mL to 50 mL THF. After approximately 2 days, the purified THF was vacuum distilled and stored under argon. 2-bromoisobutyrl bromide (2-b-b) was vacuum distilled under nitrogen and stored in a glovebox under argon prior to use. Triethylamine (Et₃N) was purified using approximately 10 wt % of calcium hydride. This solution was stirred uncapped for 24 hours and then capped and kept stirring at room temperature until used. Prior to use, Et₃N was vacuum distilled under nitrogen and stored in a glovebox under argon.

The synthesis of poly(hexyl methacrylate)-grafted nanoparticles (PHMA-g-SiO$_2$) is as follows:

Scheme 4

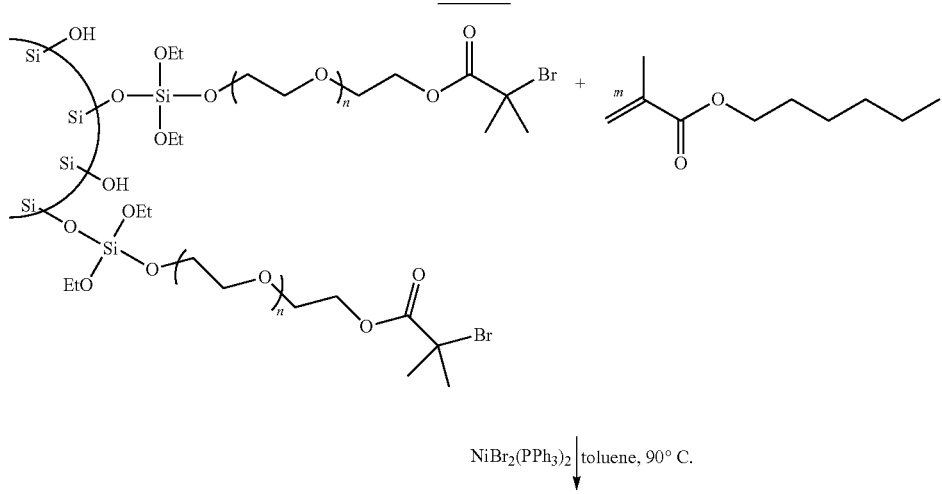

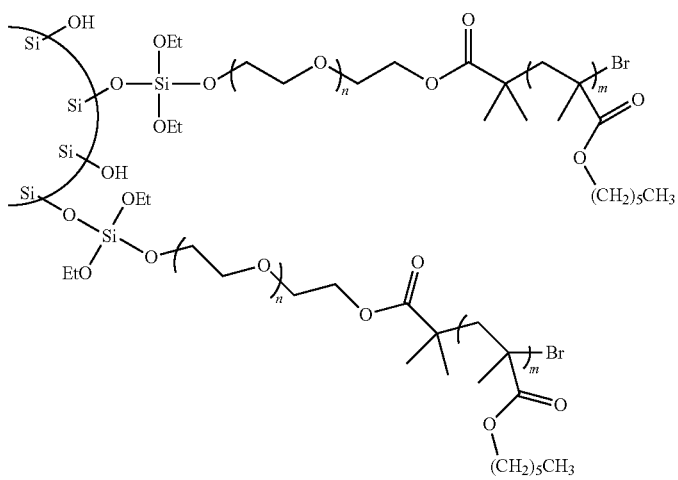

Toluene was purified with approximately 10 wt. % calcium hydride. This solution was stirred for 24 hours and then capped, covered with parafilm and stored at room temperature. Toluene was distilled and placed in a glovebox under argon. Immediately prior to use, hexyl methacrylate was stirred over $CaH_2$ for 24 hours then vacuum distilled and placed in a glovebox under argon. The functionalized $SiO_2$-peo-2bb solution was added to a round bottom flask. To this flask purified toluene, dibromobis triphenyl phosphine and hexyl methacrylate were added. The flask was capped with a rubber septum and attached to a nitrogen line equipped with a bubbler to allow for solvent evaporation. The flask was placed in a 90° C. oil bath for 10 hours. After 10 hours, the reaction was exposed to oxygen to deactivate the catalyst and then placed in the refrigerator to inhibit further polymerization.

The nickel catalyst was removed through a column of neutral alumina and distilled until a small amount of solvent remained. The solution was dialyzed in chloroform for 3 rounds of solvent changes totaling approximately 36 hours. After dialysis, the solution was placed in a 100 mL media bottle and put in a vacuum oven at 60° C. The resulting NOHMS were stored capped at room temperature. The preparation of $SiO_2$—PEG-PAN Nanoparticle-Organic Hybrid Molecules (NOHMS) occurred as follows:

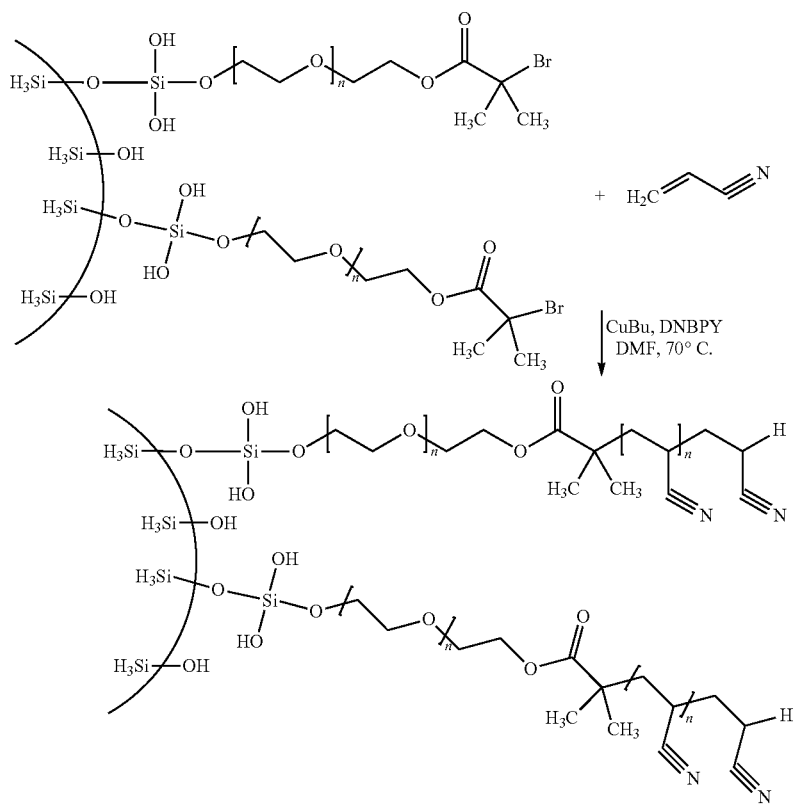

ATRP synthesis of PAN was carried out using a procedure similar to Leiston-Belanger et al., *Macromolecules*, 39(5), 1766-1770, (2006). N,N-dimethylformamide (DMF) was distilled and placed in a glovebox under argon. Immediately prior to use, acrylonitrile was purified with activated basic aluminum oxide then vacuum distilled and placed in a glovebox under argon.

In a glovebox, under argon, the functionalized $SiO_2$-peo-2bb solution was added to a round bottom flask. To this flask purified DMF, copper (I) bromide, 4,4'-dionyl-2,2'-dipyridyl (DNBPY), and acrylonitrile were added. The flask was capped with a rubber septum and placed in a 70° C. oil bath for 20 hours. After 20 hours, the reaction was exposed to oxygen to deactivate the catalyst and then placed in the refrigerator to inhibit further polymerization.

The copper catalyst was removed through a column of basic alumina and distilled until a small amount of solvent remained. The solution was dialyzed in chloroform for 3 rounds of solvent changes totaling approximately 36 hours. After dialysis, the solution was placed in a 100 mL media bottle and put in a vacuum oven at 60° C. The resulting NOHMS were stored capped at room temperature.

To characterize the molecular weight of the polymer chains, it is desirable to detach them from the $SiO_2$ cores. A HF etching process, which is known to be highly selective for Silica, was used. 300 mg of NOHMS were mixed with $NH_4.HF$ and stirred for 24 hours at room temperature. The polymer was then extracted from the solution via separation with toluene. The toluene layer was washed with distilled water 4 times and then removed with rotary evaporation.

Thermogravimetric analysis (TGA) was carried out from room temperature to 550° C. using a TA Instruments Q500 under an atmosphere of nitrogen at heating rate of 10° C./min. TGA shows the percentage of weight remaining in the samples as a function of temperature and the derivative weight loss. The remaining mass after heating to 550° C. indicates presence of inorganic material.

The TGA results display drastic changes in the degradation temperatures of the tethered PEO-PAN copolymer as compared to the pure polymers. PEG has a degradation temperature of 400° C. and pure PAN has a degradation temperature of 150° C. while the PEG-PAN tethered to a silica nanoparticle displays two degradation peaks at 270° C. and 425° C. which correspond to the PAN block and PEG block, respectively. The rise in degradation temperature of the two blocks is a confirmation of the block nature of the copolymer as well as evidence that a charred layer of PAN is forming on the outside of the nanoparticle which must be burned through before the next layer of PAN-b-PEG can be degraded.

DSC was performed using a T. A. Instruments Q1000TA Modulated Differential Scanning calorimeter under an atmosphere of nitrogen. Samples were heated at a rate of 5° C./min from room temperature to 110° C. during cycle 1, cooled at a rate of 10° C./min from 110° C. to −100° C. during cycle 2, and heated at a rate of 5° C./min from −100° C. to 110° C. during cycle 3. DSC results show several important features of the $SiO_2$—PEG-PHMA samples. First, the presence of only one glass transition temperature around −55° C. indicates the presence of a block copolymer. Had this sample been a mixture of PEG and PHMA, two distinct glass transitions would have be seen: one near −5° C. for PHMA and one near −40° C. for PEG. Second, the results show a peak near 25° C. that may be contributed to the melting of the polymer. Third, these results clearly show a minimum around 60° C. This minimum is due to crystallization of the polymer.

DLS measurements were done on Malvern Instruments Zetasizer Nano. Each sample was suspended in chloroform and filtered through a 0.45 um PTFE filter into a glass cuvette.

DSC and DLA show that the samples have a high concentration of NOHMS with diameters around 11 nm. with some particles being larger. These large particles are not numerous enough to affect the volume vs. size plot, but do to their large size affect the intensity vs. size plot. These results show that these samples are narrowly dispersed.

FT-IR experiments were performed using a Thermo Scientific iZ10. A background sample was taken before each sample. A total of 64 scans were run per sample.

GPC experiments were done using a Waters 717 plus Autosampler and a Waters 515 HPLC pump with tetrahydrofuran as the eluent. Samples were made 24 hours prior to characterization to a concentration of 1 mg/ml and allowed to equilibrate on a mechanical shaker.

An analysis of the GPC elugrams pertaining to the kinetics study of the MPEG-2bb-PHMA demonstrated that 98% conversion is achieved after 20 hours. The ATRP technique yields a bimodal distribution for moderate conversions of PHMA as evidenced by overlapping peaks that were seen between 16 and 23 ml. of elution volume of the 5 hour sample. However, as the reaction is allowed to progress, the polymer blend became less polydisperse as the PHMA conversion increases. The result reveals a narrowing of the polymer distribution from a polydispersity of 1.605 at 5 hours 1.222 for the 25 hour sample.

The elugrams indicate that the ATRP synthesis follows a living polymerization scheme, and the initial bimodal distribution can be attributed to the polydisperse nature of the MPEG as no effort was made to rigorously separate the MPEG reagent. An analysis of the GPC elugram for the PAN indicates a living polymerization scheme resulting in a fairly monodisperse sample that achieves 98% completion at 15 hours.

Rheology experiments were done using an Anton Parr Physica MCR 300 rheometer with an electrically controlled oven. Depending on the sample, the fixtures used were either a cone and plate fixture of diameter 6 mm or a cone and plate fixture of diameter 10 mm. Prior to running the experiments, the gap was zeroed at each temperature, followed by sample loading, a 30 min rest, a preshear to erase thermal history, and a 2 hour rest.

Example 8

Figure 8:
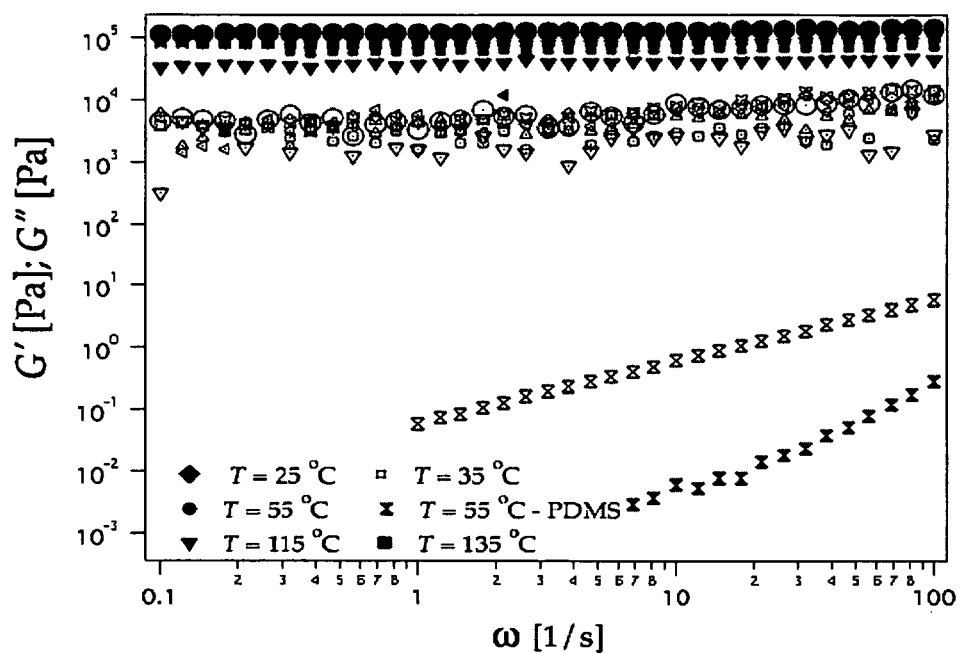
FIG. 8 shows the dynamic storage (G', filled symbols) and loss (G", open) moduli as a function of frequency and temperature for SiO$_2$-PDMS NOHMs (d$_p$=18 nm; s≈3 nm$^{-2}$) and free/untethered PDMS (M$_w$≈5 k) corona.
Figure 9:
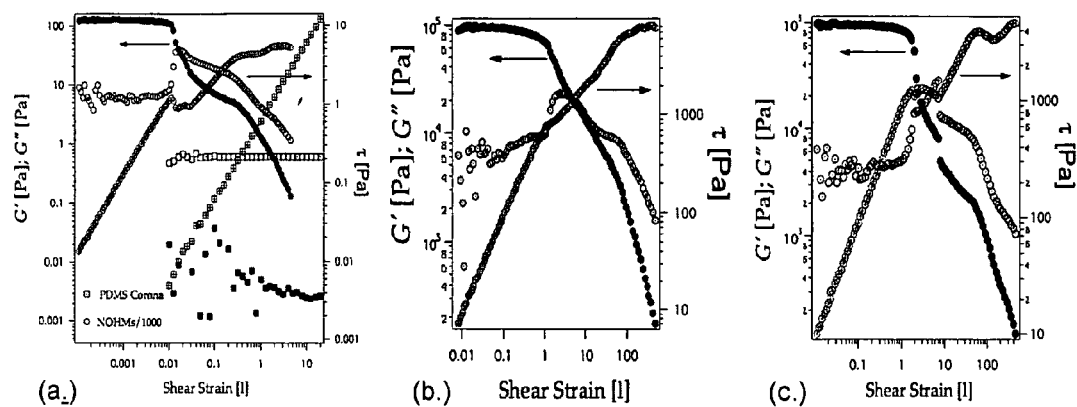
FIG. 9 shows the Storage (G') and loss (G") moduli versus shear strain, g for SiO$_2$—PDMS NOHMs with d$_p$=18 nm., s≈3 nm$^{-2}$, and corona M$_w$5 k: (a.) T=55° C.; (b.) T=25° C.; (c.) T=75° C.

A NORM is produced having a PDMS organic polymeric corona. NOHMs based on oligomeric PDMS corona possess at least four attributes that are desirable in a high-performance lubricant. First, they are homogeneous soft solids down to the length scale of their nanoscale building blocks. Second, NOHMs manifest rate-independent and weakly temperature-dependent shear moduli (G') that are many orders of magnitude greater than the shear modulus of the untethered PDMS corona (see FIG. 8). Third, even without any efforts at optimization, coatings of $SiO_2$—PDMS NOHMs on silicon exhibit a velocity-independent friction coefficient $\mu \approx 6.4 \times 10^{-3}$ at room temperature, which is comparable to the COF of our most slippery hyperbranched (PDMS) brushes. FIGS. 9(a)-9(c) are the corresponding results for the $SiO_2$—PDMS NOHMs material used for the frequency-dependent, dynamic rheology measurements in The figure clearly shows that whereas the unattached PDMS corona (squares) exhibit simple fluid like rheology (G">G'≠f (g)), the rheology of the NOHMs is again consistent with expectations for a soft glass. For the PDMS NOHMs, however, the initial increase in G", corresponding decrease in G', and slope change in t(g) are more abrupt. FIGS. 9(b) and 9(c) indicate that the sharpness of the yielding transition is temperature-dependent, with signatures of a slip-stick like transition at the highest temperature. It is believed that these behaviors reflect greater levels of interpenetration of corona chains at higher temperatures, and arise from interfacial slip between tethered chains.

Example 9

Figure 10:
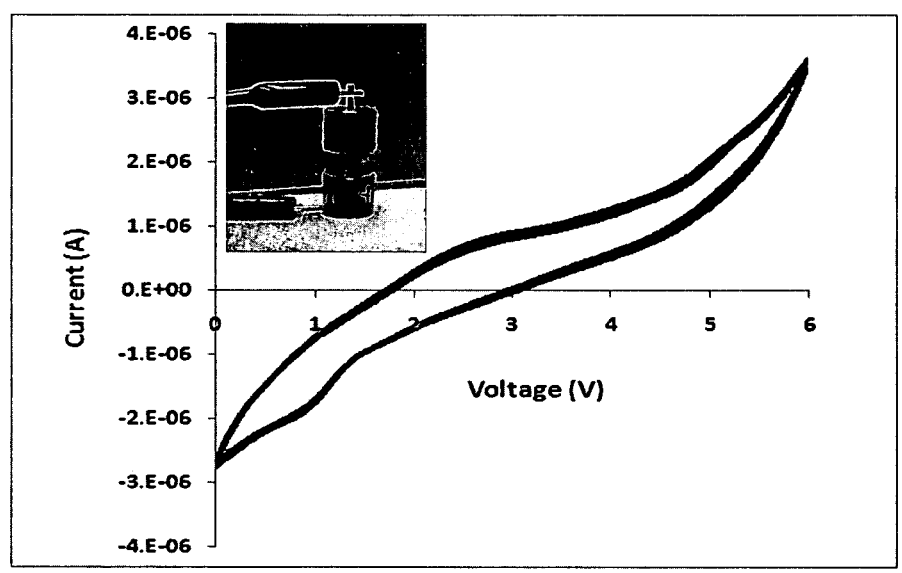
FIG. 10 is a cyclic voltammagram (CV) for SiO$_2$-MPEG NOHMs with fc=0.33, as 1 M LiClO$_4$ electrolyte. Measurements were performed at room temperature using a symmetric swage-lock type (top photograph) Li cell at a scan rate of 15 mV/s.

$SiO_2$—PEG NOHMs are produced as discussed above and doped with 1 M $LiClO_4$ to obtain an electrolyte. A rechargeable battery, comprising: (i) the electrolyte, (ii) a lithium metal anode, and (iii) a lithium metal cathode. The electrolyte is disposed between the electrodes without the need for a separator. FIG. 10 reports current-voltage data from cyclic voltammetry experiments. The experiments were repeated four times. The measurements were carried out in a symmetric swage-lock type lithium cell employing a $SiO_2$—PEG NOHMs/1M $LiClO_4$ as electrolyte. The figure shows that the material produces a working cell, which exhibits repeatable CV traces even after measurements at voltages up to 6 V (the highest studied) This stood true after each experiment.

What is claimed:
1. A nanoparticle organic hybrid material (NOHM), comprising an organic polymeric corona having a molecular weight in a range of 100-50,000 g/mol covalently attached to an inorganic nanoparticle core and a second organic polymeric corona attached to an inorganic nanoparticle core, wherein the second organic polymeric corona is composed of a different polymer from that of the organic polymeric corona, wherein in the absence of a solvent the NOHM exists as a self-suspended suspension and exhibits liquid-like properties, wherein the NOHM has a volume fraction $f_c$ of the inorganic particle ranging from about 0.05 to 0.75, and wherein the NOHM does not have ionic bonds.

2. The NOHM according to claim 1, wherein the organic polymers comprising said organic polymeric corona have a molecular weight in one of the following ranges 100-25,000 g/mol; 100-15,000 g/mol; 100-10,000; 250-7,500 g/mol; 500-7,500 g/mol; 500-5,000 g/mol; 250-5,000 g/mol; 250-1,500 g/mol; 100-2,500 g/mol; and 100-1,000 g/mol.

3. The NOHM according to claim 1, wherein the organic polymeric corona is polyethylene carbonate (PEC), polypropylene carbonate (PPC), poly(cis-1,4-isoprene) (PI), polyethylene vinyl acetate (PEVA), polyvinyl chloride (PVC), poly(ethylene glycol) (PEG), poly(ethylene oxide) (PEO), polyoxyethylene (POE), polydimethylsiloxane (PDMS), poly-alpha-olefin (PAO), polyvinylidene fluoride (PVDF), PEG-PS diblock copolymer, or a combination thereof.

4. The NOHM according to claim 1, wherein the inorganic nanoparticle core is selected from the group consisting of a metal salt, metal oxide, and metal.

5. The NOHM according to claim 1, wherein the inorganic nanoparticle core is $SiO_2$, $SnO_2$, $Fe_2O_3$, $Fe_3O_4$, $Co_3O_4$, MgO, SrO, BaO, CaO, $TiO_2$, $ZrO_2$, FeO, $V_2O_3$, $V_2O_5$, $Mn_2O_3$, NiO, CuO, $Al_2O_3$, $SiO_2$, ZnO, $Ag_2O$, Mg, Sr, Ba, Ca, Ti, Zr, Fe, V, Mn, Fe, Ni, Cu, Al, Si, Zn, Ag, Au, Co, or a mixture thereof.

6. The NOHM according to claim 1, wherein the inorganic nanoparticle core is selected from the group consisting of a multi-lobed nanoparticle, cubed-shaped nanoparticle, conductive nanoparticle, hollow nanoparticle, a nanoshell, quantum dot, nanocrystal, magnetic nanoparticle, a metal and a nanorod.

7. The NOHM according to claim 1, wherein the volume fraction $f_c$ is greater than 0.10 and less than 0.50.

8. An electrolyte, comprising the NOHM according to claim 1 and an ionic dopant.

9. The electrolyte according to claim 8, wherein the organic polymeric corona of the NOHM is doped with $LiCF_3SO_3$, $LiN(CF_3SO_2)_2$, $LiC(CF_3SO_2)_3$, $LiC(CH_3)(CF_3SO_2)_2$, $LiCH(CF_3SO_2)_2$, $LiCH_2(CF_3SO_2)$, $LiC_2F_5SO_3$, $LiN(C_2F_5SO_2)_2$, $LiB(CF_3SO_2)_2$, $LiPF_6$, $LiClO_4$, $LiI$, $LiBF_4$, $LiSCN$, $LiAsF_6$, $NaCF_3SO_3$, $NaPF_6$, $NaClO_4$, $NaI$, $NaBF_4$, $NaAsF_6$, $KCF_3SO_3$, $KPF_6$, $KI$, $LiCF_3CO_3$, $NaClO_3$, $NaSCN$, $KBF_4$, $Mg(ClO_4)_2$, $Mg(BF_4)_2$, or a combination thereof.

10. The electrolyte according to claim 8, wherein the organic polymeric corona is a polyethylene oxide or polyethylene glycol corona doped with $LiClO_4$, $LiPF_6$, $LiCF_3SO_3$, $LiAsF_6$, or $LiN(CF_3SO_2)_2$, and wherein the inorganic nanoparticle cores are selected from the group consisting of titania, $SiO_2$, $SnO_2$, $Fe_2O_3$, $Fe_3O_4$, and $Co_3O_4$.

11. The nanoparticle organic hybrid material of claim 1, wherein the organic polymeric corona has end groups selected from nitroxy, alkene, alkyne, epoxy, ethylene oxide, chloride, bromide, amine, sulfonic acid, hydroxyl carboxyl, anhydride, fluorine, sulfonate esters, amino, hydrazido, mercpato, carbonate, carbamate, chlorinate, cyanuryl chloride, epoxide, aldeyhde, and siloxane.

12. A composition comprising a first nanoparticle organic hybrid material (NOHM) and a second NOHM, each of the first NOHM and the second NOHM comprising an organic polymeric corona having a molecular weight in a range of 100-50,000 g/mol covalently attached to an inorganic nanoparticle core, wherein the second NOHM has a different organic polymeric corona or inorganic nanoparticle core than the first NOHM, wherein in the absence of a solvent the first NOHM and the second NOHM exist as self-suspended suspensions and exhibit liquid-like properties, wherein the first NOHM and the second NOHM have a volume fraction $f_c$ of the inorganic particle ranging from about 0.05 to 0.75, and wherein the first NOHM and the second NOHM do not have ionic bonds.

* * * * *